(12) United States Patent
Skrabal et al.

(10) Patent No.: US 7,783,345 B2
(45) Date of Patent: Aug. 24, 2010

(54) IMPEDANCE-BASED MEASURING METHOD FOR HEMODYNAMIC PARAMETERS

(75) Inventors: Falko Skrabal, Graz (AT); Jürgen Fortin, Graz (AT)

(73) Assignee: CNSystems Medizintechnik GmbH, Graz (AT)

( * ) Notice: Subject to any disclaimer, the term of this patent is extended or adjusted under 35 U.S.C. 154(b) by 1539 days.

(21) Appl. No.: 11/101,358

(22) Filed: Apr. 7, 2005

(65) Prior Publication Data
US 2005/0177062 A1 Aug. 11, 2005

Related U.S. Application Data

(63) Continuation of application No. PCT/AT03/00302, filed on Oct. 7, 2003.

(30) Foreign Application Priority Data
Oct. 7, 2002 (AT) ................ A 1517/2002

(51) Int. Cl.
*A61B 5/05* (2006.01)
(52) U.S. Cl. ............ 600/547; 600/508; 600/536
(58) Field of Classification Search ........... 600/508, 600/509, 547, 536
See application file for complete search history.

(56) References Cited

U.S. PATENT DOCUMENTS

| | | | |
|---|---|---|---|
| 3,730,171 A * | 5/1973 | Namon | 600/526 |
| 3,996,925 A * | 12/1976 | Djordjevich | 600/506 |
| RE30,101 E * | 9/1979 | Kubicek et al. | 128/713 |
| 4,450,527 A | 5/1984 | Sramek | |
| 4,807,638 A | 2/1989 | Sramek | |
| 4,947,862 A | 8/1990 | Kelly | |
| 4,951,682 A | 8/1990 | Petre | |
| 5,000,753 A | 3/1991 | Hagen et al. | |
| 5,063,937 A | 11/1991 | Couch et al. | |
| 5,086,781 A | 2/1992 | Bookspan | |
| 5,109,870 A | 5/1992 | Silny et al. | |
| 5,114,424 A | 5/1992 | Hagen et al. | |
| 5,335,667 A | 8/1994 | Cha et al. | |
| 5,505,209 A * | 4/1996 | Reining | 600/547 |
| 6,125,297 A * | 9/2000 | Siconolfi | 600/547 |

FOREIGN PATENT DOCUMENTS

JP 3504202 T 9/1991

* cited by examiner

*Primary Examiner*—Carl H Layno
*Assistant Examiner*—Brian T Gedeon
(74) *Attorney, Agent, or Firm*—Panitch Schwarze Belisario & Nadel LLP

(57) ABSTRACT

A method is provided for measuring the volume, the composition and the movement of electroconductive body fluids, based on the electrical impedance of the body or a body segment, especially for performing electromechanocardiography (ELMEC) or impedance cardiography (IKG) measurements for determining hemodynamic parameters. According to the method, an alternating measuring current of at least one frequency is introduced into the body, and the impedance and temporal variations thereof of essentially the same body segment through which the alternating measuring current flows are measured for at least two different measuring lengths (L, L2, L3, L4, L5), essentially in the longitudinal direction of the body.

31 Claims, 8 Drawing Sheets

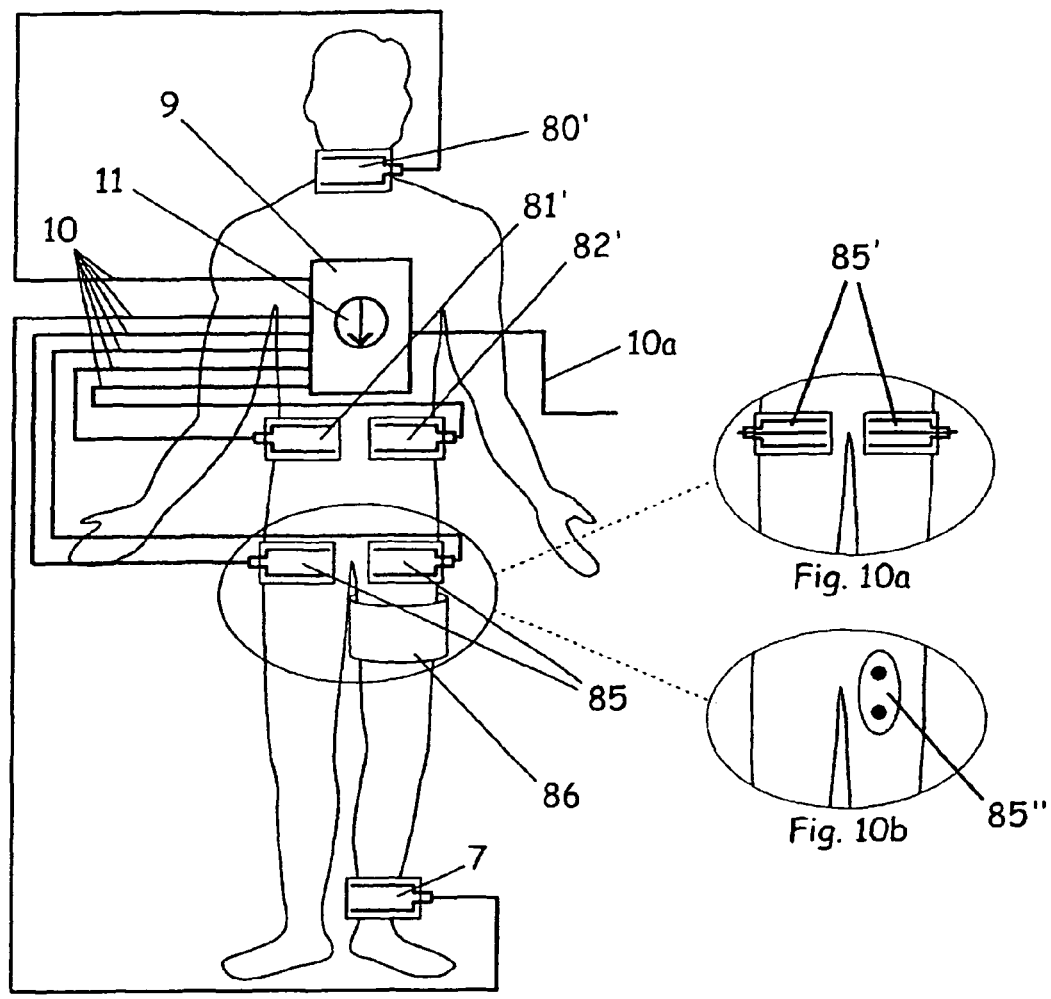
Fig. 10a
Fig. 10b
Fig. 10
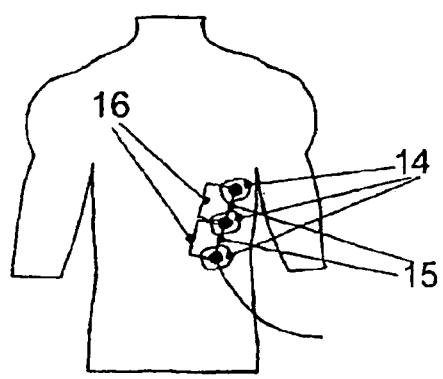
Fig. 11

IMPEDANCE-BASED MEASURING METHOD FOR HEMODYNAMIC PARAMETERS

CROSS-REFERENCE TO RELATED APPLICATIONS

This application is a continuation of International Application No. PCT/AT2003/000302, filed Oct. 7, 2003, which was published in the German language on Apr. 15, 2004 under International Publication No. WO 2004/030535, and the disclosure of which is incorporated herein by reference.

BACKGROUND OF THE INVENTION

The invention relates to a non-invasive method for measuring the volume, the composition and the movement of electroconductive body fluids, based on the electrical impedance of the body or a body segment, especially for performing electromechanocardiography (ELMEC) or impedance cardiography (IKG) measurements for determining hemodynamic parameters, wherein an alternating measuring current of at least one frequency is introduced into the body by measuring electrodes applied to the body surface.

In medical practice, it is often necessary to measure cardiac mechanical activity. There are different methods, such as echocardiography, for measuring stroke force, inotropism, contractility and ejection fraction. In addition, the amount of blood a heart ejects in one heartbeat, stroke volume and other hemodynamic parameters are frequently determined. If the heart rate is known, cardiac output (cardiac output=cardiac output per minute=CO) may thus be calculated. From these values cardiac function may be derived, which in turn is a basis for the diagnosis of heart diseases and new physiological findings. However, echocardiography is not really appropriate for monitoring patients with serious heart diseases in ICUs or during anesthesia because it requires the permanent presence of medical personnel. Since this constitutes a serious problem, medics have numerous other methods at their disposal for determining CO.

One such method comprises the introduction of a catheter into the pulmonary artery and/or into the aorta, where by means of an indicator value or substance, which may be heat, cold, sodium chloride or lithium, a drop of said indicator substance within a measuring distance may be determined, followed by the determination of CO according to the Fick principle. A disadvantage of this method concerns the introduction of a catheter into a human vessel and complications resulting therefrom, such as bleeding and infections. Consequently, this invasive method involves high costs with regard to disposable catheters and high risks for patients. See Dalen, J. E, "The Pulmonary Artery Catheter—Friend, Foe, or Accomplice?" *JAMA*, 286(3): 348-350 (Jul. 18, 2001); Polanczyk C. A. et al., "Right Heart Cathertization and Cardiac Complications in Patients Undergoing Noncardiac Surgery" *JAMA*, 286(3): 309-314 (Jul. 18, 2001). The principle of thermodilution or dye dilution is also susceptible to errors so that usually an average of several measurements is required to obtain a plausible result. Furthermore, physical strain or other conditions resulting in body temperature variations also yield wrong results in thermodilution.

Recently it has been attempted to use the Flick principle to determine cardiac output by measuring gases in alveolar air. This is made possible by the quick gas exchange between blood and alveolar air so that the concentration in these two media can practically be equated. If a gas is added to alveolar air, its blood concentration increases as well, and if the gas addition is stopped, gas content decreases in the blood as well as in the alveolar air, wherein according to the Fick principle, CO can be calculated from the concentration decrease within a given time unit.

One method that has proven especially successful is $CO_2$ rebreathing. Here, a loop is introduced into the patient's respiratory tract, and the patient rebreathes his own exhaled air for a particular period of time to increase $CO_2$ concentration in the blood. A disadvantage of this method is that the patient has to wear a mouthpiece and keep his respiration rather steady to guarantee a constant concentration of breathing gases in the alveolar air and the blood. Therefore, this method is mainly used during anesthesia which guarantees a steady tidal volume and a steady respiratory rate. With spontaneously breathing patients, there remains the disadvantage of respiration through a tube system with a mouthpiece, which considerably increases respiratory dead space and airway resistance, and consequently also breathing effort. Furthermore, the method's accuracy decreases significantly with spontaneous breathing. Another method for measuring CO consists in a similar technique where instead of $CO_2$ an inert gas is used, which is inhaled and also quickly equilibrates in the blood.

Another method involves the determination of stroke volume and other hemodynamic parameters from the pulse form, which is sensed at a peripheral artery. Pulse form variations are partly due to changes of stroke volume and other hemodynamic parameters, which allows an indirect derivation of changes of stroke volume and other hemodynamic parameters by means of a transfer function. This method, however, requires calibration by one of the above techniques at the beginning and is not sufficiently accurate. Another well-known method relates to the transcutaneous measurement of an indicator substance, such as indigo green, at the capillaries of an ear or finger, which, however, significantly reduces the accuracy of the Fick principle.

Another method well known in the art is impedance cardiography (IKG). In this method, a constant alternating electric field is applied to the thorax, and the alternating voltage variation caused by the alternating electric field indicates a change of thoracic fluid content. More particularly, with this method resistance to alternating current (impedance) is measured, which is a measure for the change of thoracic fluid content. The change of the thoracic fluid content, on the other hand, is a measure for the amount of blood ejected per stroke. From stroke volume and other hemodynamic parameters (SV) and the heart rate (HR), cardiac output (CO=SV*HR) can be calculated.

Usually a pair of electrodes leading a current to the body is attached above or at the upper limit and below or at the lower limit of the thorax. Between this pair of electrodes, a second pair of electrodes is attached for measuring the resulting alternating current. The inner pair of electrodes must be kept at a particular distance so that the upper voltage electrode is positioned at least at glottis level, and the lower electrode at xiphoid level. The distance between the two electrodes also depends on the thorax length and is hereafter called electrode measuring length L. Impedance is calculated according to the following formula: $Z(t)=u(t)/I_0$, where u(t) is the changing alternating current and $I_0$ is the alternating current constant effective current intensity impressed into the body.

So far, either circular electrodes or spot electrodes similar to ECG electrodes have been used for this purpose. Austrian patent application A 392/2001, filed on Mar. 13, 2001, by J. Fortin et al. for "Medical Electrode" describes a new electrode arrangement, where two strip electrodes run parallel to each other over a short distance on the same sheet, their distance from each other being exactly preset by the common carrier sheet and reproducible. One of these parallel strip electrodes mounted on the common carrier sheet serves for the application of the measuring current, the other parallel strip electrode is intended for sensing the measuring voltage. The upper pair of electrodes (or double electrode) can be positioned, for example, at the neck, the lower pair of electrodes left and right, respectively, at the inferior thoracic aperture. This electrode arrangement shows much better reproducibility of results than former circular electrodes and the spot electrodes described in the U.S. Pat. No. 4,450,527 of Sramek for "Noninvasive Continuous Cardiac Output Monitor," see FIG. 1a+FIG. 1b.

Disadvantages of the above impedance technique relate to the fact that the results are calculated according to the Kubicek equation (Kubicek, W. G., et al., "Development and Evaluation of an Impedance Cardiac Output System," *Aerospace Medicine* 37, 1208-1212 (1966); and "The Minnesota Impedance Cardiograph—Theory and Applications," *Biomed. Eng.*, 9(2): 410-416 (1974)) or the Sramek equation (U.S. Pat. No. 4,450,527 of Sramek et al.; Sramek, B., "Noninvasive Continuous Cardiac Output Monitor"; Sramek, B., "Noninvasive Technique for Measurement of Cardiac Output by Means of Electrical Impedance," *Proceedings of the Vth ICEBI*, Tokyo (1981); and Sramek, B. et al., "Stroke Volume Equation with a Linear Base Impedance Model and Its Accuracy, as Compared to Thermodilution and Magnetic Flowmeter Techniques in Humans and Animals, *Proceedings of the Vth ICEBI*, Zadar, Yugoslavia, p. 38 (1983)), respectively, both being based on strongly simplified assumptions about the human body. These assumptions are only partly true, which leads to considerable errors in the calculation of stroke volume and other hemodynamic parameters as well as of cardiac output.

Equation 1 shows the Kubicek equation for calculating stroke volume and other hemodynamic parameters from a variation of the impedance signal:

$$SV = \rho * \frac{L^2}{Z_0^2} \cdot LVET \cdot (dZ/dt)_{max} \tag{1}$$

Herein, L is the measuring length in cm between two electrodes on the body surface, $\rho$ is the resistivity of the blood in $\Omega$ cm, $Z_0$ is the base impedance in $\Omega$, $(dZ/dt)_{max}$ is the maximum of the first derivative of electrical resistance and impedance variations with respect to time in $\Omega$/sec by cardiac activity and LVET, left ventricular ejection time in sec.

As can be seen, the electrode measuring length L enters the equation as a quadratic value, wherein, at present, this electrode measuring length is determined on the thorax surface.

Furthermore, blood resistivity $\rho$ is a linear value in the formula, which means that blood resistivity mainly depends on the blood's content of red blood cells. According to the law by Lamberts, R. et al., "*Impedance Cardiography*," Van Gorcum, Assen, Holland (1984)], $\rho$ can be approximately calculated from the hematocrit Hct by means of the formula $$\rho = 71.24 \cdot e^{0.000358 \, Hct\,power\,2} \tag{2}$$

or estimated by means of a similar formula or, in other methods, simply kept constant. What is not taken into account here is that blood conductivity is not only influenced by the hematocrit, but also by the ionic concentration in plasma as well as proteins contained therein. Therefore, an empirically determined equation, which takes into account only one and not all blood components, will never give the exact conductivity or resistance of blood. Furthermore, blood conductivity is also influenced by the flow rate, since with higher velocity erythrocytes are oriented lengthwise and consequently increase fluid cross section. With even higher velocities and resulting turbulences, blood resistance can increase even further.

The formula according to Sramek uses 17% of standing height instead of the electrode measuring length, since it has been empirically shown that thorax length corresponds approximately to 17% of total body length. Another assumption in this formula is the divisor 4.25, which arises from an estimated relation between electrode measuring length and waist circumference as well as an estimated constant relation between a cylindrical thorax model and a truncated-cone thorax model (see U.S. Pat. No. 4,450,527, column 5, line 50ff). Body length H therefore even enters the formula as a cubic value.

$$SV = \frac{(0.17 \cdot H)^3}{4.25} \cdot LVET \cdot \frac{(dZ/dt)_{max}}{Z_0} \tag{3}$$

Bernstein, D. P. et al. (see "A New Stroke Volume Equation for Thoracic Electrical Bioimpedance: Theory and Rationale," *Critical Care Medicine*, 14: 904 to 909 (1986)) "corrected" this formula by multiplying the above formula by a correction factor $\delta$.

$$\delta = \beta(W_{real}/W_{ideal}) \tag{4}$$

wherein $\beta$ is a blood volume index, and $W_{ideal}$ and $W_{real}$ are the ideal and real weights of an individual.

The ideal weight for men is $$W\,ideal = 0.534H - 17.36 \tag{5}$$

The ideal weight for women is $$W\,ideal = 0.534H - 27.36 \tag{6}$$

Herein, H is the standing height in cm.

This shows that in all equations different measuring units are mixed. Consequently, the resulting equations have nothing to do with correctly derived, credible mathematics. By introducing anthropometric values into such an equation, indirect measures for stroke volume and other hemodynamic parameters of the heart of healthy individuals are directly involved in the calculation of stroke volume and other hemodynamic parameters. In individuals with healthy hearts, CO shows a perfect relation to the body surface. Consequently, the formula contains a parameter which has nothing to do with the measurement of stroke volume and other hemodynamic parameters, i.e. the patient's body measurements. Based on standing height and resulting electrode measuring length L between glottis and xiphoid, tall patients therefore automatically have larger stroke volumes and higher other hemodynamic parameters than small patients. The above formula by KUBICEK directly includes a measure for body dimensions as well.

As shown in FIG. 1, the measuring length between the electrodes, when placed correctly between the superior and inferior thoracic apertures, correlates surprisingly well with the patient's height.

According to the above, in individuals without heart diseases, hemorrhagically measured stroke volume and other hemodynamic parameters correspond well with impedance cardiography results because real standing height is a measure for cardiac output. A tall and heavy individual actually has to transport much more blood to tissue within a certain time unit than a delicate individual. With heart diseases, this principle does not hold anymore so that the correlation between actual cardiac output and cardiac output measured by impedance cardiography is bad or not existent because body measurement values introduced into the formula loose their significance. In individuals with heart diseases, this leads to an enormous bias towards normal and thus incorrect high values.

Additionally, values determined by impedance cardiography are distorted in the wrong direction, that is towards too high CO values, because of the following phenomenon. Due to their illness, patients with cardiac insufficiency usually have more body fluid in their thorax than individuals with healthy hearts. The increased thoracic fluid content reduces base impedance $Z_0$ in Q by nature. This value enters the respective calculation formula in an inverted (Sramek) or quadratically inverted form and gives CO values that are too high, which can lead to fatal diagnostic errors. In individuals with healthy hearts, $Z_0$ is a measure for thorax geometry, which is not the case in patients with increased thoracic fluid content.

This is illustrated in FIG. 2. Here the ejection fraction EF was measured echocardiographically according to the Simpson technique in patients with and without cardiac insufficiency and compared with CO. The echocardiographic parameter EF was used instead of echocardiographically measured CO because this value can be determined much more accurately. As can be seen, there is no relation between CO and ejection fraction, a relation that would, however, be expected to exist if impedance cardiography was a suitable method for cardiac insufficiency.

Consequently, impedance cardiography has not really become accepted by cardiologists, at least in Europe, because correspondence with the actual stroke volume and other hemodynamic parameters may be good in individuals with healthy hearts, but in individuals with heart diseases, where the results are really decisive for diagnosis, accurateness is rather poor. In the United States, the technique has nevertheless been increasingly used because it has been shown that relative changes of stroke volume and other hemodynamic parameters can thereby be monitored rather conveniently so that effects of pharmacological interventions can be determined very well, even if the absolute values are wrong.

Furthermore, none of the apparatus currently available on the market is able to provide results for stroke volume and other hemodynamic parameters or CO without first entering standing height or thorax length between the electrodes, i.e. a different measure for standing height. Especially in intensive care units, a patient's weight and height can often not be measured or asked for. Entering a wrong value, which in practice can happen easily, would even further distort the results.

An apparatus or a method for measuring cardiac output should, however, be able to give reliable results without a priori knowledge about standing height and weight, as is the case with the gold standard of thermodilution and other methods using the Fick principle, for example the $CO_2$ rebreathing technique or other breathing gas methods. As soon as a priori knowledge about body measurements is used, the measuring results are pushed into the direction where the CO value should be, i.e., a bias is introduced into the equation that simulates good results of the respective method in individuals with healthy hearts. Furthermore, in case of electrically measured cardiac output only electrically measured parameters should be introduced into an equation.

U.S. Pat. No. 4,450,527 describes an apparatus for impedance measurements where the dimensions of the thorax, especially the measuring length between the electrodes, where the measurements are conducted, have to be determined and entered. Thorax impedance is measured as a function of time and effects caused by respiration movements are eliminated so that the patient can breath normally during the measurement process. Spot electrodes for current impression as well as sensing of a measuring voltage are positioned in the neck area and sternum area. The measuring length between the lower and upper electrodes is not changed during the measurement.

U.S. Pat. No. 5,109,870 describes a catheter for measuring motility and peristalsis in tubular organs, e.g. the esophagus, by simultaneous, multiple impedance measurements, which catheter includes an insulating plastic tube, annular electrodes and interior channels for electrode leads. The annular electrodes are connected to impedance transformers which convert the measured signals into voltage or current signals so that they can be displayed. Due to this multiple electrode arrangement a simultaneous measurement of a plurality of measuring channels is possible in order to draw conclusions with regard to movement and transport characteristics of the organ being measured. For this purpose the catheter has to be inserted into the organ and fixed therein in a particular position. Even for patients in good health condition, this measuring method is rather strenuous and can therefore not be repeated arbitrarily often. Cardiac output is not determined with said method.

U.S. Pat. No. 4,951,682 discloses a cardiac catheter for measuring cardiac output by means of a plurality of spaced ring electrodes. In the introduction (column 2, second paragraph), this document mentions non-invasive techniques for obtaining cardiac output and holds that these have severe limitations and that invasive measurements by means of cardiac catheters show decisive advantages. Only invasive cardiac catheter measurements are mentioned, which by nature cannot be repeated very often on one patient and may entail serious complications.

U.S. Pat. No. 4,947,862 describes a device for the measurement of the amount of body fat on a patient by a applying high-frequency current to the body and sensing a voltage. It comprises magnitude and phase detection circuits for measuring the magnitude and phase of the produced voltage signals with reference to the impressed current. Here, standing height, weight and age have to be determined and entered into an input device, wherein measuring errors relating to these values enter the calculation of the amount of body fat.

Finally, U.S. Pat. No. 5,063,937 discloses a multiple frequency measurement system for determining bioimpedance of a patient's body over a large frequency range, wherein errors in the determination of the measuring length between the electrodes are not taken into consideration.

BRIEF SUMMARY OF THE INVENTION

It is thus an object of the present invention to provide a method as mentioned in the beginning, particularly for determining stroke volume and generally for measuring other hemodynamic parameters, such as inotropism or ejection fraction, by means of impedance cardiography, which helps to overcome the above disadvantages.

According to the present invention this is achieved by introducing an alternating measuring current of at least one frequency into the body and by measuring the impedance and temporal variations thereof essentially of the same body segment through which the alternating measuring current flows for at least two different measuring lengths, essentially in the longitudinal direction of the body.

By measuring the impedance and its variation for two different measuring lengths, the actually electrically participating "operational body segment length" and the actually participating electrically "operational body segment volume" and the actually measured "operational resistivity" of the blood can be electrically determined by solving equations with several unknowns, or this additional information can, with empirically determined equations, be entered into a so-called "black box" model, into which only electrically measured values are entered. Consequently, the dependence on body measurements and other information of the body is eliminated.

Since impedance changes in the thoracic area have special significance in the determination of cardiac output, and since it has proven advantageous to change the electrode measuring length in the main flow direction of blood, a further aspect of the present invention consists in that the impedance is sensed at the thorax close to the inferior and superior thoracic apertures for at least two different measuring lengths of essentially the same body segment.

Another embodiment of the invention, where the impedance is measured on the trunk near the upper and lower ends of the trunk for at least two different measuring lengths on essentially the same body segment, has the advantage that additionally the impedance of the extremities can be measured over two different distances, providing an operational length and an electrically participating volume, respectively, for this area as well.

Introduction of the measuring current at the thorax or trunk area leads to current antinodes in the body interior, while usually a strongly linear current propagation is preferable for the measurement, which can be achieved by current introduction at the extremities. Another embodiment of the invention may comprise the introduction of a current at or close to the lower body end instead of the inferior thoracic aperture as well as impedance measurements at the thorax and/or at the trunk and/or at the extremities, and that for two different measuring lengths.

In the determination of some hemodynamic parameters or parameters concerning fluid balance, it may be an advantage to additionally measure whole-body impedance, i.e. impedance between the lower and upper body end. This additional measurement of whole-body impedance is not only applicable to the method of the present invention, but also to any other conventional impedance cardiography measuring method, and it is therefore claimed independently of the measuring method of the present invention with different electrode measuring lengths, i.e. also with regard to known prior art categories of methods.

Maximum accuracy and reproducibility of impedance measurements are also provided if the difference between the two different measuring lengths is small compared to the length of the measured body part, especially if the ratio of the length of the examined body part to the length difference is 3:1 to 50:1, most preferably approximately 10:1.

In impedance measurements on the body, an alternating measuring current may be impressed by means of current electrodes spaced from each other on the body surface by a current electrode measuring length, and a measuring voltage produced by the measuring current may be sensed by means of voltage electrodes spaced from each other on the body surface, especially the thorax surface, by a voltage electrode measuring length, whereafter the electrical impedance and variations thereof may be calculated from the measuring current and the measuring voltage.

An embodiment of the invention can comprise the calculation of an operational electrode measuring length or, if necessary, also an operational distance between electrodes from the impedance values determined for different measuring lengths between electrodes. Based on these values actually effective in the body, a reliable determination of the impedance or variations thereof may be achieved. Consequently, variations of the electrode measuring length do not have to be determined manually anymore.

This allows the calculation of the electrically operational length of the body segment from the formula $L_0 = d/(Z_{02}Z_{01} - 1)$, where d is the difference between the two electrode measuring lengths used for the measurement, $Z_{02}$ is the impedance for the longer electrode measuring length, and $Z_{01}$ is the impedance for the shorter electrode measuring length.

In order to avoid asymmetric current distribution in the patient's body, another embodiment may comprise the provision of voltage electrodes at the inferior thoracic aperture as double electrodes on the left and right side, respectively, of the thorax, wherein electrodes positioned at the same distance in the longitudinal direction are electrically connected to each other.

Alternatively, it can be provided that the electrodes on the left and right side, respectively, of the thoracic aperture may selectively be switched off.

When positioning measuring electrodes on the trunk, an advantageous embodiment of the method of the present invention consists in the provision of voltage electrodes at the lower end of the trunk as double electrodes on the left and right side, respectively, of the lower end of the trunk, wherein the electrodes positioned at the same distance in the longitudinal direction are electrically connected to each other. Consequently, the measurement may include a relatively large body volume. Here, the electrodes on the left and right lower end of the trunk, respectively, may selectively be switched off.

The provision of at least one further current electrode and/or voltage electrode results in a change of the electrode measuring length of the current electrodes and/or voltage electrodes with respect to another electrode element, preferably in the longitudinal direction of the body, and thus in the main flow direction of the blood, so that the measurement of the impedance or temporal variations thereof in the thorax can be conducted simultaneously or sequentially for the shorter and longer electrode measuring length. This change of the electrode measuring length L should be constant, known or calculable.

In an above-mentioned method, objects of the present invention may also be achieved by measuring the electrical impedance at two or more measuring frequencies and determining the portions of the intra- and extracellular spaces, followed by the use of these values for the calculation of stroke volume and other hemodynamic parameters. This method can, independently of the defined change of measuring length of the present invention, also be applied in a conventional two-electrode system or in combination therewith. By choosing the two measuring frequencies, the property of blood to show different resistances at different frequencies can be used for determining different hemodynamic parameters depending on blood resistivity.

The number of different frequencies applicable to the method of the present invention is not bounded above, and a continuous sweeping of a frequency band, preferably from a lower measuring frequency to a higher measuring frequency, lies within the scope of the invention, wherein the lower measuring frequency according to a preferred embodiment of the invention is approximately 1 kHz and the higher measuring frequency approximately 1000 kHz at most.

A phase angle between measuring current and measuring voltage at different frequencies may also be a measure for the determination of hemodynamic parameters.

An advantageous embodiment of the present invention may comprise the simultaneous measurement of the electrical impedance or impedance variations with respect to time at two measuring frequencies. The two frequencies can, for instance, be separated by a frequency filter (frequency multiplexer). Alternatively, several measuring frequencies can be measured alternately within very short time frames. From the different impedance values, which may be measured at different frequencies, body fluid distribution can be determined, which allows conclusions with regard to thorax geometry.

Another embodiment of the method of the present invention may comprise the measurement of the impedance at three different frequencies, wherein the different frequencies are 1 to 10 kHz, 30 to 100 kHz and more than 200 kHz.

As mentioned above, one of the problems of impedance cardiography consists in the determination of blood resistivity, which plays a role in several calculation formulas for hemodynamic parameters. Since the determination of the maximum temporal derivative of impedance with respect to time at increasing frequencies is a measure for blood resistivity, the objects of the present invention may be achieved by determining maximum temporal variation of the measured impedance values (dZ/dt) at least two different measuring frequencies, and by determining therefrom the resistivity of the blood present in the body. Such a measurement may be conducted with or without changing the measuring length between the voltage or current electrodes.

From the impedance changes, for instance at a high and at a low measuring frequency, a ratio may be calculated, which is a measure for the erythrocytes deformed in the aorta by acceleration. From this ratio, another parameter may be derived by appropriate mathematical signal analysis, which parameter is of importance for the calculation of stroke volume.

According to an improved embodiment of the present invention, the maximum temporal variation of the measured impedance value, especially in relatively small time frames, at different times of the cardiac cycle may thus be determined. This leads to a time average of impedance value changes over the cardiac cycle.

The determination of mean values from extreme values of a cardiac cycle may, according to a further embodiment of the present invention, be achieved by setting the time slots at an abrupt rise of resistivity and at the time of minimum blood flow at the end of a diastole.

If time slots are put over the entire cardiac cycle in the form of small floating time slots, the accuracy of the method of the present invention may be increased.

Finally, an important advantage of the method of the present invention is that empirical equations that have been determined by means of a gold standard, such as the Fick principle for stroke volume or echocardiography or isotope methods for other parameters, such as ejection fraction, pulmonal wedge pressure, diastolic function and the like, may be used for measuring hemodynamic parameters, underwater weighing or DXA techniques, and dilution techniques for body fluid. These empirical equations can, for instance, be obtained by means of partial correlations and multiple regression equations, or by means of neural networks or other "machine learning" methods.

When using two spaced voltage electrodes, the measuring voltage for the first voltage electrode measuring length and for a second voltage electrode measuring length differing from the first one are determined, and from the measurement values the operational length for impedance determination is determined in contrast to a reference electrode.

In order to be able to determine the distance between the voltage electrodes by measuring electrical quantities, another embodiment of the present invention provides for the determination of the measuring voltage for a third voltage electrode measuring length differing from the first and second ones.

Furthermore, by positioning electrodes at the periphery or at the extremities or at the upper and lower body end, whole-body impedance at different frequencies as well as body fluid with its fractions, such as extracellular space and intracellular space, may be determined, and the relation between body fluid and electrically participating thoracic volume allows further conclusions with regard to actual stroke volume and other hemodynamic parameters. If additionally measurements with different frequencies are conducted at the extremities, the intracellular space and extracellular space may be determined, and these values as well as their relation to each other can be introduced into an equation for calculating cardiac output. Since intracellular space and extracellular space show characteristic variations in individuals suffering from heart diseases, further conclusions with regard to cardiac function may be drawn. Cardiac insufficiency, for instance, leads to a decrease of intracellular space and an increase of extracellular space.

Another embodiment of the present invention may comprise the impression of the measuring current by means of two current electrodes at the upper and lower end, respectively, of a body extremity, for instance a leg, e.g. an ankle, and/or an arm, e.g. a wrist.

All substances involved in the impedance measurement on the body depend on the frequency, which may provide important information on the constitution of the organism to be measured.

Consequently, the measuring current should be impressed at different measuring frequencies, and the according measuring voltage values and temporal variations thereof, especially during a cardiac cycle, should be determined. Frequencies used herein should result in a measurable variation of blood impedance values.

An advantageous signal-to-noise ratio in the determination of the measuring values may be achieved by impressing, according to a further embodiment of the present invention, the measuring current over several different voltage electrode measuring lengths and at several different measuring frequencies, followed by the determination of the measuring voltage caused by the measuring current.

Furthermore, it may be advantageous for the determination of the impedance character (inductive or capacitive) to determine the phase angle between measuring current and measuring voltage.

Furthermore, the use of amplitudes, areas, and ascending or descending tangents of the impedance waves B, C, X and O independently or together is advantageous for calculating hemodynamic parameters.

Another variant of the method of the present invention may comprise the determination of the sodium content in serum and its use in the calculation of relevant parameters.

Furthermore, the sodium concentration in serum may be mathematically estimated by the method of the present invention and obtained as a result.

Additionally, hormones, such as ADH and natriuretic peptide, especially the atrial natriuretic hormone, the brain natriuretic peptide and precursors thereof regulating body fluids, fractions and the composition thereof, may be estimated by the method of the present invention by means of empirical equations and obtained as a result.

Using modern communication means, data obtained by the method of the present invention may be processed by sending the results in digital form to a central station, preferably by telephone or e-mail, where they are further processed and assessed, whereafter all necessary measures and therapy changes are transmitted to the patient from a remote place.

Furthermore, the invention is related to an apparatus for measuring electrical impedance or temporal variations thereof in a human body, especially for performing electromechanocardiography or impedance cardiography (IKG) measurements for determining hemodynamic parameters.

According to the present invention, the above object of the invention is achieved by providing two voltage electrodes, at least one of which is provided as a double voltage electrode element, wherein the impedance and temporal variations thereof between the two voltage electrodes may be sensed.

By providing the voltage electrode in the form of a double voltage electrode element having two electrodes spaced from each other in a known distance, the difference between two electrode measuring lengths with regard to the other voltage electrode is predefined so that an operational electrode measuring length may be determined from two measuring voltages sensed at the double voltage electrode.

An embodiment of the double voltage electrode element adaptable to the body shape may be obtained by attaching the at least one double voltage electrode element to a common insulating carrier sheet.

In a further embodiment of the invention, at least one of the voltage electrodes comprising a triple electrode element may consist of a current electrode and two voltage electrodes. When implementing the method of the present invention, the introduction of an alternating measuring current and the sensing of measuring voltages may thus be conducted at a single electrode element. More particularly, the current electrode and the double voltage electrode element may be fixed to a common carrier sheet as a triple electrode element.

In order to allow impedance measurements according to the present method without manual replugging or switching, the invention may provide that all electrode element terminals are brought together in a distribution element by means of connecting leads, and that the distribution element is connected to measuring lines and control lines of a measuring device.

Another possibility to automate the method of the present invention may comprise a controllable distribution element so that the electrode elements are connectable to different measuring lines and control lines of the measuring device.

Since the impedance values measurable by means of the measuring system of the present invention depend on the position of the respective human body in space, it is advantageous to record the angle between the longitudinal body axis and the horizontal or perpendicular. Another embodiment of the measuring system of the present invention may provide for an angle meter for measuring body inclination. Preferably, it is positioned on the distribution element.

Furthermore, the present invention relates to a medical electrode element for measuring the electrical impedance or temporal variations thereof in a human body, especially for performing electromechanocardiography or impedance cardiography (IGK) measurements for determining hemodynamic parameters, by means of a first current electrode, which has an electrical terminal for impressing an alternating measuring current, and a first voltage electrode spaced therefrom, which has a voltage terminal for sensing an electrical measuring voltage, wherein at least one further voltage electrode is provided with a voltage terminal, and wherein the at least one further voltage electrode is/are positioned in a distance from the first voltage electrode, for implementing the method of the present invention, wherein the first voltage electrode as well as the at least one further voltage electrode are provided as parallel, electroconductive strips and the widths of the strips are equal to, preferably smaller than, the distance between the strips.

The provision of strip-shaped electrodes leads to a relatively high measuring volume, e.g. within the thorax, whereby significant measurement results for the determination of body impedance may be obtained.

In contrast to the conventional four point method (two current electrodes and two voltage electrodes), here a further voltage electrode and optionally a further current electrode are provided, which are placed on the body in a way to make sure that the attachment of these additional voltage and/or current electrodes results in a change of the measuring length L between the voltage electrodes or the current introduction sites of at least two electrode elements placed on the patient's body, preferably in the longitudinal direction of the body and thus in the main flow direction of blood, so that simultaneous or sequential measurements of the impedance and temporal variations thereof in the body segment may be examined—for the shorter as well as the longer measuring length between the respective electrodes.

By introducing further degrees of freedom, i.e. different measuring lengths between the voltage electrodes and live electrode pairs, the actually electrically participating "operational thorax length" and the actually participating electrical "operational" thorax volume and the actually measured "operational resistivity" of the blood, respectively, may be electrically determined by solving equations with several unknowns, or this additional information can, with empirically determined equations, be entered into a so-called "black box" model. Consequently, only electrically measured values enter this formula. The problem of standing height, i.e. that stroke volume and other hemodynamic parameters can only be correctly determined in healthy individuals based on advance anthropometric information, is thereby eliminated.

In another embodiment, the at least one further voltage electrode is formed by a second voltage electrode, which is positioned in a known, constant or calculable distance (d) from the first voltage electrode.

Thus, the measuring voltage towards a reference voltage, which is introduced into a different body area, may be sensed at the first voltage electrode as well as at the second voltage electrode, and based on the known distance d between the first and the second voltage electrodes, an operational measuring length for the reference voltage electrode for impedance determination may be calculated from the obtained measuring values.

The distance d between the first and second voltage electrodes is known due to the design of the electrode element of the present invention, however, it has proven advantageous to additionally determine an operational distance between the first and second voltage electrodes in line with the determination of an operational measuring length.

According to another embodiment of the present invention, this may be achieved if the at least one further voltage electrode consists of the second voltage electrode and a third voltage electrode, the third voltage electrode being positioned in a distance from the first voltage electrode.

It has been shown that the use of strip electrodes provides a high level of reproducibility of the values measured by means of the electrode element of the present invention if the ratio of strip length to distance between electrodes is in the range between approximately 2, preferably 4, and approximately 15, preferably 10.

According to a further embodiment of the invention, the distance between individual electrodes may be kept constant by positioning the first voltage electrode and the first current electrode as well as the at least one further voltage electrode and/or the at least one further current electrode on a common, electrically insulating carrier material.

The carrier material may consist of a carrier sheet, wherein the first voltage electrode and the first current electrode as well as the at least one further voltage electrode and/or the at least one further current electrode are secured on one side of the carrier sheet and preferably provided with an electroconductive adhesive layer. Thus, a constant spacing of the individual electrodes on the body surface can be guaranteed during the implementation of the method of the present invention.

In another embodiment of the present invention, the carrier material may comprise a plurality of sheet strips with adhesive surfaces, onto which the first voltage electrode and the first current electrode as well as the at least one further voltage electrode and/or the at least one further current electrode are attached, the sheet strips with the electrodes secured thereon being able to adhere to a common base carrier sheet in a substantially parallel arrangement, wherein the base carrier sheet may be pulled off from the body surface after the attachment of sheet strips thereto. After pulling off the base carrier sheet, only the sheet strips with one electrode each remain adhered to the patient's body and are in electrical contact with the body surface. While thereby a constant spacing of the individual electrodes is maintained, the small total contact surface results in a clear reduction of skin irritations so that the electrodes can be kept in longer contact with the patient.

In order to achieve a reliable and easy-to-handle connection to the leads required for the operation of the electrode elements of the present invention, in another embodiment of the present invention, the carrier sheet may on one longitudinal end be tapered to a plug-type surface, on which the first voltage electrode and the first current electrode as well as the at least one further voltage electrode and/or the at least one further current electrode are closely spaced.

In another embodiment, the first voltage electrode and the first current electrode as well as the at least one further voltage electrode and/or the at least one further current electrode are provided in the form of spot electrodes spaced from each other by means of spacers, such as another carrier sheet, a tensioned band or cable, or rigid spacers. In this way, impedance measurements may be conducted on very small contact areas on the body surface.

Furthermore, the invention relates to a measuring system for measuring electrical impedance and temporal variations thereof in a human body, especially for performing impedance cardiography (IKG) measurements for determining hemodynamic parameters, by means of an alternating measuring current source and a first voltage measuring device as well as a medical electrode element of the present invention, the measuring current source being connectable to the current electrode and the voltage measuring device being connectable to the first voltage electrode of the electrode element.

In measuring systems for measuring electrical impedance in a body currently in use, the measuring length between two electrode elements for impedance measurements or at least the patient's standing height have to be determined, e.g. by means of a tape measure. Measuring inaccuracies and the fact that the actually electrically operational measuring length differs significantly and unpredictably from the distance between the individual electrodes, which distance is to be measured on the body surface, lead to measurement errors and inaccuracies.

It is thus an object of the present invention to provide a measuring system as described above which overcomes the above problems.

The present invention achieves this object by providing a selector switch which connects the voltage measuring device either to the first voltage electrode or to the at least one further voltage electrode. Alternatively, the measuring system may also provide for a simultaneous measurement for different measuring lengths.

From the known distance between the first and the further voltage electrode, the actual measuring length towards a reference electrode may be determined, which is used for the determination of the impedance by means of the impressed current and the sensed voltage values.

Since the results of impedance measurements on the patient's body depend on the frequency, in an improved embodiment of the present invention the alternating measuring current source can have a, optionally continuously, variable measuring frequency. Thus, the effects of body components such as blood, tissue and bones on the measurement results at different measuring frequencies can be determined.

In this connection, a phase detector for determining the phase angle between the measuring current of the measuring current source and the measuring voltage measured by the voltage measuring device may be provided in order to gain another measurement value from the phase angle.

Since the different impedance values, which can be determined by the measuring system of the present invention, depend on the position of the human body in space, it is advantageous to record the angle between the longitudinal body axis and the horizontal or perpendicular. Another embodiment of the present measuring system may provide for an angle meter for measuring body inclination. This can preferably be positioned in a distribution element.

The measuring electrodes of the present invention may also be used for other purposes, wherein it seems to be advantageous to connect the electrode elements according to another embodiment of the invention to an ECG measuring device.

Since the electrode element of the present invention described herein and the accordingly implementable method of the present invention have no great resemblance to current impedance cardiography, we propose the new term "multi site frequency electromechanocardiography (msf-ELMEC)" for the method and measuring system of the present invention described herein, which allow for the determination of all determinable parameters of cardiac function, such as stroke volume, inotropism, ejection fraction, diastolic cardiac function, valve alterations, and potential other hemodynamic parameters, e.g. pulmonary pressure, and other important parameters, such as volume, distribution and composition of different body compartments.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 10 is another schematic view of an embodiment of the measuring system of the present invention;

FIG. 10a is a detailed view of an improved embodiment of the measuring system of FIG. 10;

FIG. 10b is a detailed view of an improved embodiment of the measuring system of FIG. 10;

FIG. 11 is a schematic view of another embodiment of the measuring system of the present invention;

DETAILED DESCRIPTION OF THE INVENTION

Figure 1:
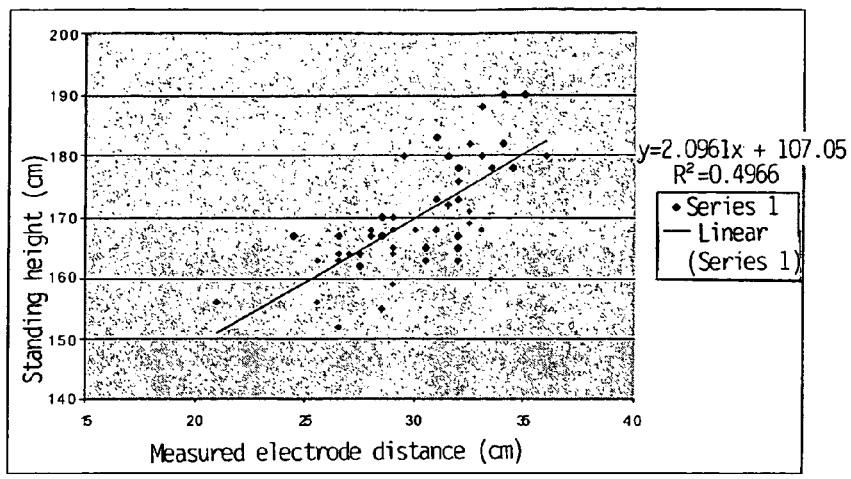
FIG. 1 is a graph showing the correlation between the patient's height and the measured distance between the electrodes when place correctly between the superior and inferior thoracic apertures.
Figure 2:
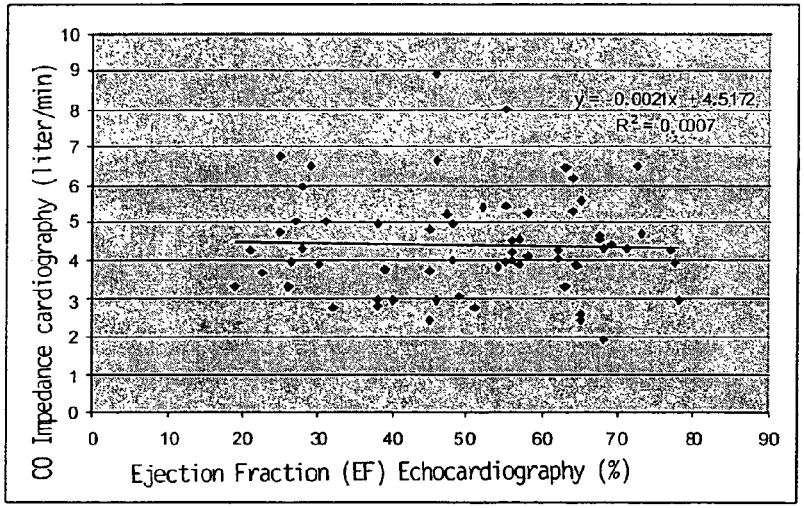
FIG. 2 is a graph showing no relation between cardiac output (CO) measured by impedance cardiography and ejection fraction (EF) measured by echocardiography.

In the method of the present invention for measuring the volume, the composition and the movement of electroconductive body fluids, based on the electrical impedance of the body or a body segment, especially for performing electro-mechanocardiography (ELMEC) or impedance cardiography (IKG) measurements for determining hemodynamic parameters, an alternating measuring current of at least one frequency is introduced into the body, and the impedance and temporal variations thereof of essentially the same body segment through which the alternating measuring current flows are measured for at least two different measuring lengths, essentially in the longitudinal direction of the body.

More particularly, in an impedance cardiography (IKG) measurement for determining hemodynamic parameters, such as cardiac stroke volume, an alternating measuring current is impressed by current electrodes, which are spaced from each other on the body surface by a current electrode measuring length, and a measuring voltage produced by the measuring current may be sensed by means of voltage electrodes, which are spaced from each other on the body surface, especially the thorax surface, by a voltage electrode measuring length.

Based on the measuring current and the measuring voltage, the electrical impedance and temporal variations thereof are calculated.

In the method according to the invention, e.g. the measuring voltage for different voltage electrode measuring lengths between voltage electrodes on essentially the same body segment or segments is determined. From the resulting measuring voltage values, the respective impedance values are calculated. Changes of the measuring length are mainly made in the longitudinal direction of the body and thus in the main flow direction of the blood transported therein.

Furthermore, it is advantageous to determine the impedance and variations thereof at at least two different measuring frequencies, preferably at least three to four frequencies. This requires the alternating measuring current source, which is used for the measurement, to have a variable, optionally continuous, alterable measuring frequency.

Here, the measuring frequencies should be sufficiently far apart to allow for the observation of a measurable variation of blood impedance and the penetration of body membranes by the electrical current at the higher frequency. Relevant frequencies are for instance those between 1 and 10 kHz, between 30 and 100 kHz, especially approximately 40 kHz, more than 200 kHz, e.g. approximately 300 kHz to 1 MHz, these representing only general guidelines for the desired frequency range. Furthermore, it is proposed to not measure single frequencies but instead conduct a frequency sweep over the total possible frequency spectrum, from a lower measuring frequency to a higher measuring frequency, e.g. between approximately 1 kHz and approximately 1000 kHz, or over a portion of interest within this range. In order to maintain a favorable signal-to-noise ratio during the measurement, it may be advantageous to conduct alternating or simultaneous measurements for several lengths and several frequencies. Furthermore, it may be advantageous to influence the phase angle of the impedance signals by means of a special design of the electronic equipment. For this purpose, there is provided a phase detector for determining the phase angle between the measuring current from the measuring current source and the measuring voltage measured by the voltage measuring device.

As is generally known, according to the definition of resistivity impedance is $$Z_0 = \rho^*(L/A) \tag{7}$$

where $\rho$ is the resistivity of the working section, L is the measuring length and A is the cross section of the working section.

If a second working section with the measuring length $$L_2 = L + d \tag{8}$$

is provided, where d is a constant or calculable distance between the measuring lengths L and $L_2$, it can easily be derived that the operational electrical measuring length $L_0$ may be calculated according to the following formula:

$$L_0 = \frac{d}{\frac{Z_{02}}{Z_{01}} - 1} \tag{9}$$

When entering the electrically determined measuring length $L_0$ into e.g. the KUBICEK equation, all unknown measures of length in the formula are eliminated, with the exception of the difference d (distance between the electrodes), which is defined by the design of the electrodes themselves.

Figure 9:
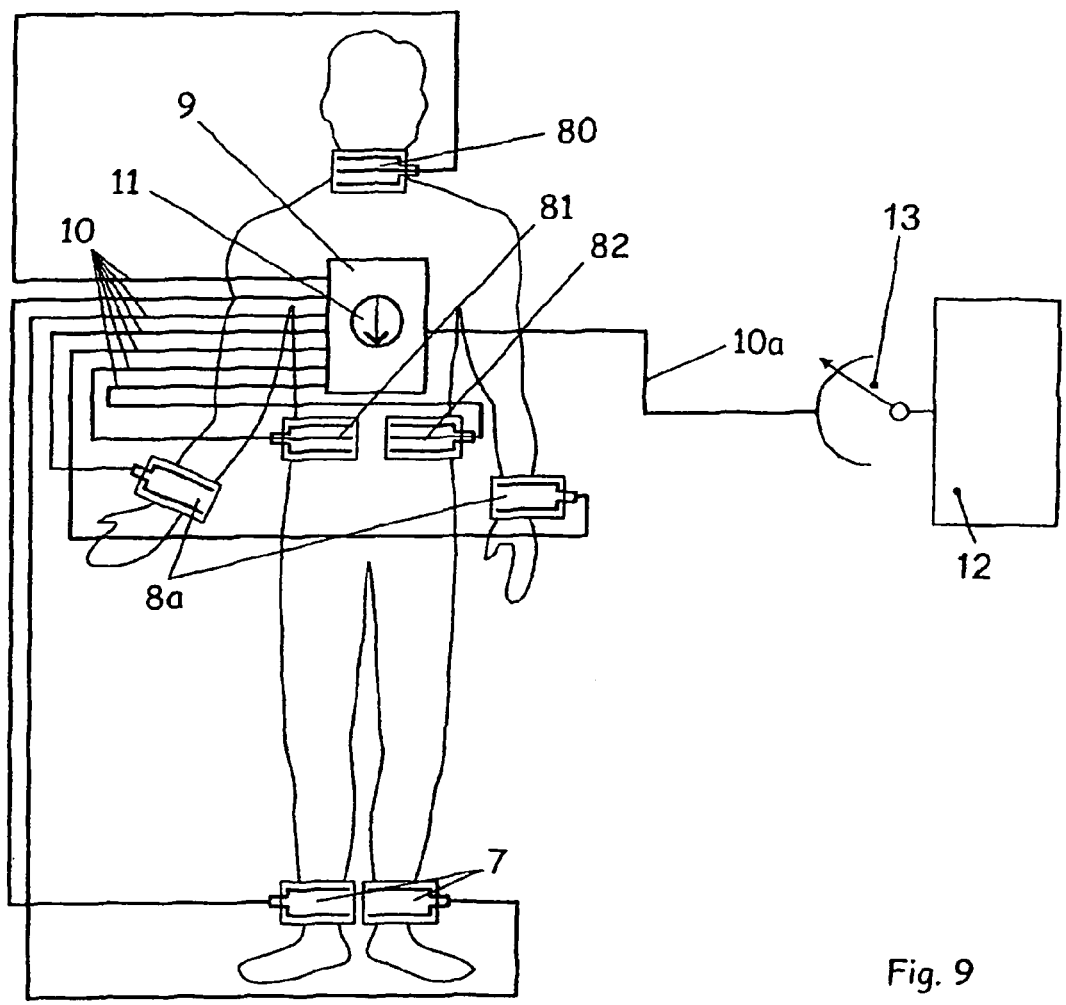
FIG. 9 is a schematic view of an embodiment of the measuring system of the present invention.

In an apparatus for measuring the electrical impedance and temporal variations thereof in a human body in order to determine body fluids, their composition and their movement in the body, e.g. hemodynamic parameters, the present invention provides two voltage electrodes 8a, 80 and 81, 82, 80', 81', 82', 85, 85', 85", 7, at least one of which is provided as a double voltage electrode element 80, 81, 82, 81', 82', 85, 85', 85", wherein the impedance and variations thereof with respect to time may be sensed between the two voltage electrodes. In FIG. 9, one voltage electrode is formed by a triple electrode element 80, and the second voltage electrode is formed by two triple electrode elements 81, 82 positioned at the same height.

Figure 7:
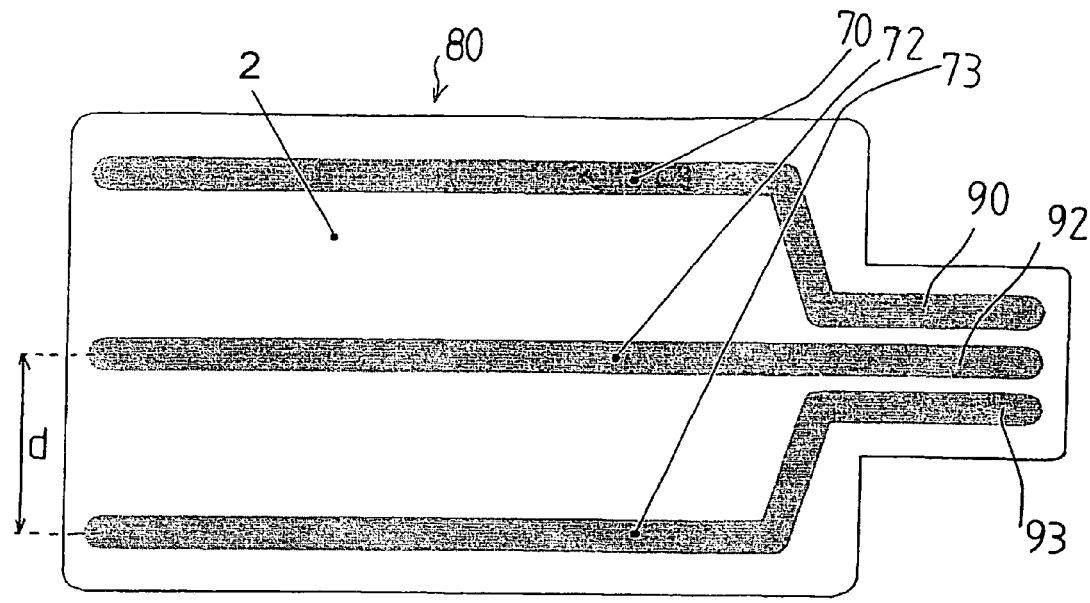
FIG. 7 is a schematic view of an embodiment of the electrode element of the present invention.

The design of the triple electrode element 80, 81, 82 consisting of a current electrode 70 and two voltage electrodes 72, 73, which form a double voltage electrode element, is shown in FIG. 7, wherein the current electrode 70 and the two voltage electrodes 72, 73 are secured in a constant and known distance, preferably on a common carrier sheet 2 to maintain the constant distance.

The difference d is known from the design of the electrodes 72, 73, which can, however, also be just as electrically invalid as the length L measured on the thorax surface. Thus, it can be advantageous to calculate an operational do by respective operation of the existing measuring electrodes in accordance with the calculation of $L_0$ by formula (9). Since it is advantageous not to intervene in the basically inhomogeneous electric field within the thorax during the calculation of these operational lengths, the live electrodes should not be altered and only additional measuring electrodes should be used.

Figure 12:
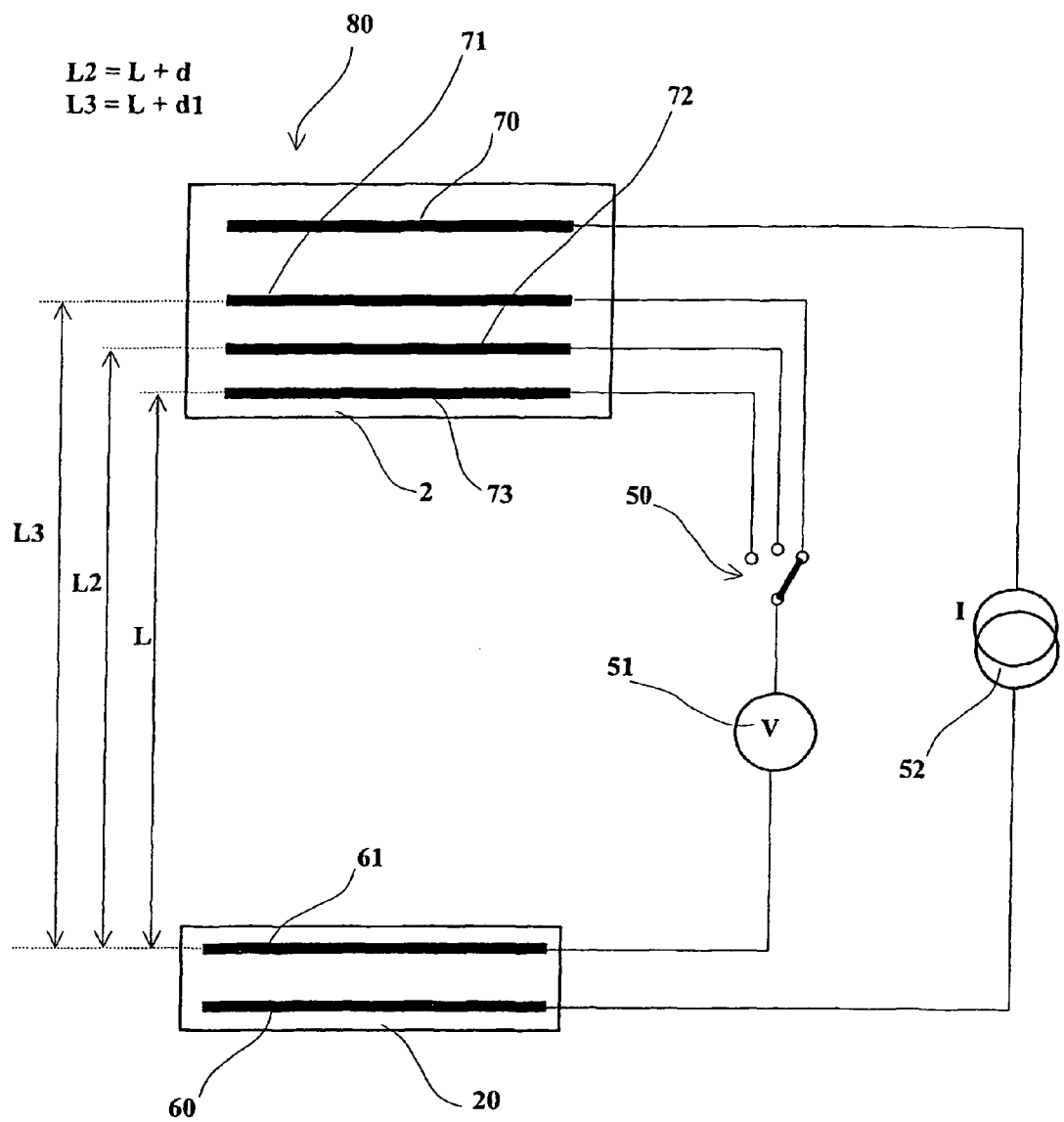
FIG. 12 is a schematic view of another embodiment of the measuring system of the present invention.

The calculation of do requires e.g. the mounting of an additional measuring electrode 71 on an electrode element 80 of the present invention, as shown in FIG. 12, so that a quadruple electrode element consisting of a current electrode 70 and three voltage electrodes 71, 72, 73 is positioned at the superior thoracic aperture. The measuring current is impressed by means of an alternating measuring current source 52, inserted between the current electrode 70 and a current electrode 60 of an electrode element 20, which is secured at the inferior thoracic aperture. If the current is impressed e.g. at the patient's lower body end 7 or at the lower trunk end 85, 85', a triple electrode element with three voltage electrodes optionally positioned either at the inferior or superior thoracic aperture is sufficient.

A voltage measuring device 51 is connected to a voltage electrode 61 of the electrode element 20 and connectable, via a selector switch 50, to either the first voltage electrode 73 or a further, i.e. the second or third, voltage electrode 72, 71. The measuring length between the voltage electrode 61 and the first voltage electrode 73 is L, the measuring length between the voltage electrode 61 and the second voltage electrode 72 is L2, and the measuring length between the voltage electrode 61 and the third voltage electrode 71 is L3. Here, L2=L+d and L3=L+d1.

By setting the select switch 50, a total of three measuring voltages corresponding to the measuring lengths L, L2 and L3 may be sensed.

After $d_0$ has been calculated, this value may be used in equation (9) instead of d.

Figure 13:
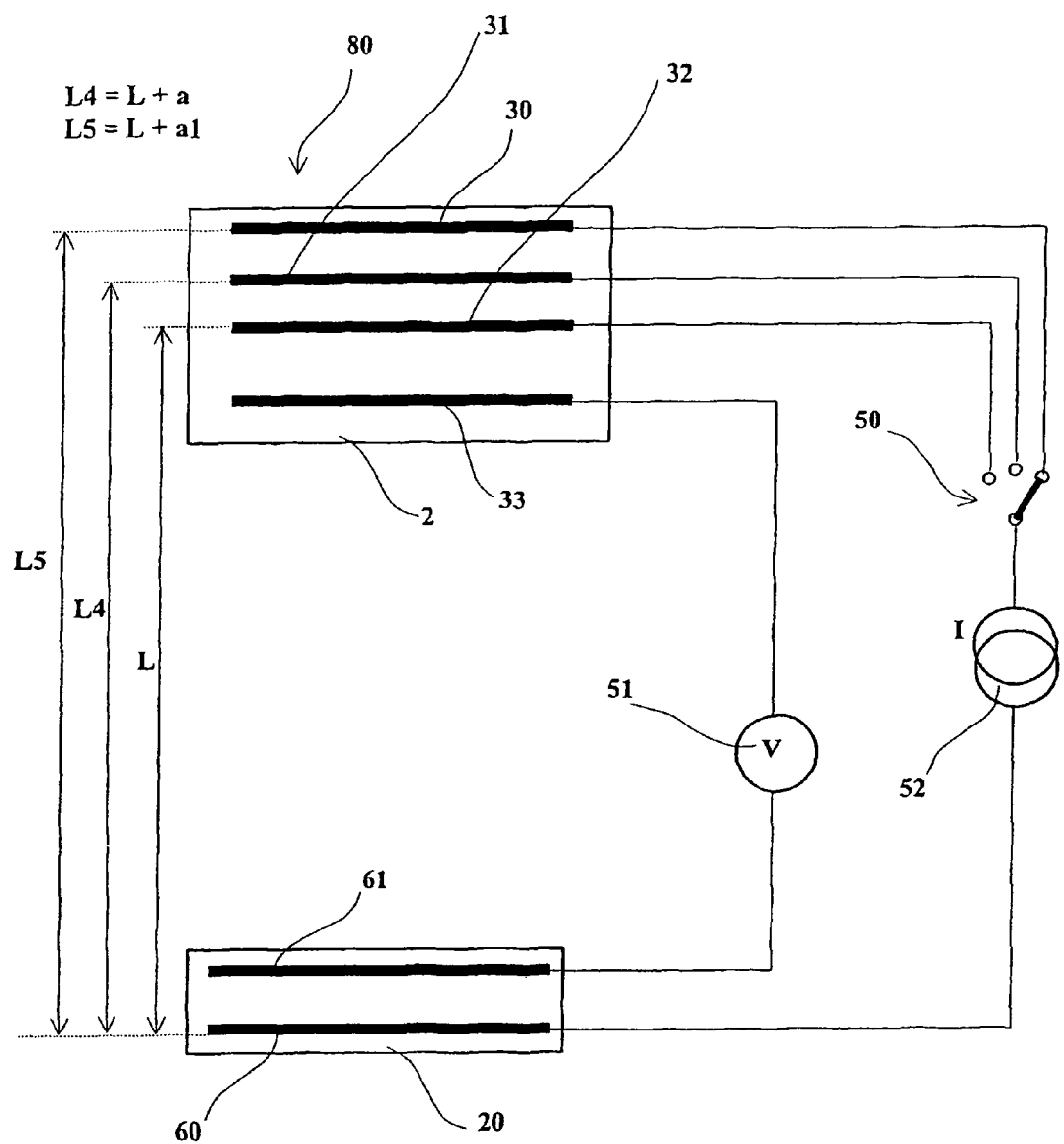
FIG. 13 is a schematic view of another embodiment of the measuring system of the present invention.

One embodiment of the measuring system of the present system, which provides for several current electrodes instead of several voltage electrodes, is shown in FIG. 13.

The starting point is again a quadruple electrode element 80, on which a voltage electrode 33 and three current electrodes 30, 31, 32 positioned in a defined distance from each other are provided. The measuring length between the current electrode 60 of the electrode element 20 and the current electrode 32 is L, for the current electrode 31 it rises to L4, and for the current electrode 30 it rises to L5, where L4=L+a and L5=L+a1.

The measuring current is impressed via an alternating measuring current source 52, which is connected to the current electrode 60 of the electrode element 20 and connectable to the current electrodes 30, 31, 32 via the select switch 50.

The voltage measuring device 51 is connected to the voltage electrode 61 of the electrode element 20 and to the voltage electrode 33 so that by means of voltage measurements for three different measuring lengths L, L4 and L5 of current impression, impedance and an operational measuring length, which is based on considerations analogous to the embodiment of FIG. 11, may be determined.

Figure 3:
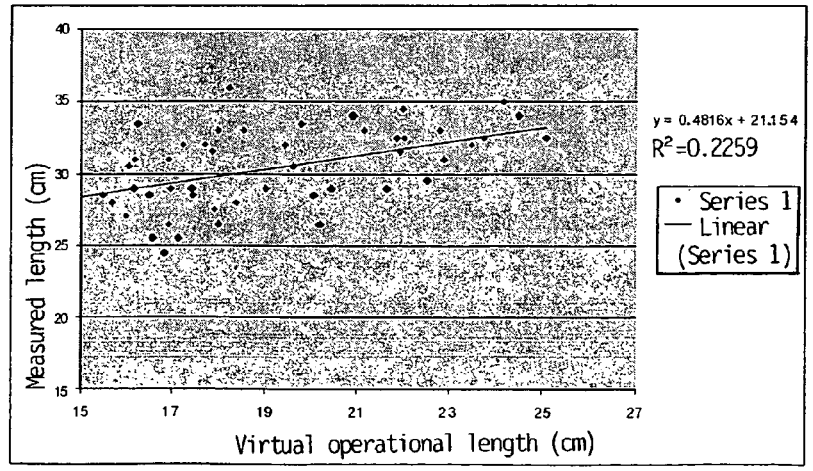
FIG. 3 is a graph showing the relation between the measuring length determined on the body and the operational measuring length determined between two voltage or current electrodes.

FIG. 3 shows the differences identified in practical experiments between the actual length measured on the body surface in cm and the "operational length" $L_O$ calculated according to Ohm's law for a state-of-the-art electrode element. As can be seen, the relation between the two lengths is rather unsatisfactory, which shows that there is no clinically relevant interrelation between the length measured on the body surface and the operational length derived from the above formula. FIG. 3 particularly shows that the measured length is considerably larger than the virtual length, which suggests that there are substantial variations in the diameters of the electrically participating thorax tissues between the electrodes, which, in the form of "electrical antinodes", obviously reduce the virtual distance between electrodes in an unpredictable manner.

This shows that impedance cardiography has so far been based on completely wrong theoretical considerations. That is easily understandable because electrical distribution in the thorax is rather inhomogeneous, and conduction through different media like skin, bones, fat, lungs, heart and vessels varies. Until now, reproducibility of impedance cardiography has been strongly limited because of these inhomogeneities. In order to achieve certain reproducibility, electrodes had to be placed on exactly the same spot on the thorax. This is possible in short-term experiments, not, however in long-term observations lasting several days or more. With the method of the present invention, dependence on the attachment site of electrodes has been eliminated because the method is always corrected by the determination of the operational measuring length, even if circumstances within the thorax have changed, e.g. due to different fluid distribution.

A particularly advantageous method provides for the attachment of the live electrode on the extremities 7, 8a because from there the current flows mainly along large vessels and along the aorta. Here, the measuring current is impressed via two current electrodes each placed at at least one body extremity, e.g. a leg and/or an arm.

Thus, a much more homogenous electric field is obtained in the thorax than with the placement of the live electrode directly on the thorax. Consequently, it would be sufficient to place a double electrode at the inferior thoracic aperture, as is described in Austrian patent specification A392/2001. The attachment of two double electrodes, e.g. an electrode as described in A392/2001 or two adjacent single electrodes, to the upper body end (e.g. neck, head, arms) or the lower body end allows for the measurement of body fluids at the same time by simultaneously determining whole-body impedance. This is important because thoracic fluid content has to be regarded in relation to the organism's fluid balance. Especially with cardiac insufficiency, the relation between fluid distribution in the thorax and total body fluid is strongly distorted, and this is the reason why until now impedance cardiography has been inapplicable for cardiac insufficiency.

Another main problem of impedance cardiography is the incorporation of blood resistivity, which should enter the formula quantitatively. Therefore, the Kubicek equation includes a blood resistivity value calculated from the hematocrit. Quail et al. (see "Thoracic Resistivity for Stroke Volume Calculation in Impedance Cardiography," *J Appl. Physiol.* (1981)) modified the Kubicek equation and calculated the resistivity from stroke volume and other hemodynamic parameters, which they determined in dogs by means of an electromagnetic flux meter (EMF):

$$\rho_{blood} = \frac{SV_{EMF} \cdot Z_0^2}{l^2 \cdot LVET \cdot (dZ/dt)_{max}} \quad (10)$$

QUAIL et al. found out that $\rho_{blood}$ is dependent on the hematocrit, but remains constant otherwise. They replaced $\rho_{blood}$ by a mean thoracic resistance $\rho_0$. If $\rho_0$ is approximately constant in Kubicek's equation, it may be replaced as follows:

$$Z = \rho \cdot \frac{1}{A} \Rightarrow \rho_0 = \frac{Z_0 \cdot A}{l} \quad (7 \Rightarrow 11)$$

This is entered into Kubicek's equation:

$$SV = \frac{Z_0 \cdot A}{l} \cdot \frac{l^2}{Z_0^2} \cdot LVET \cdot (dZ/dt)_{max} \quad a, b, c)$$

$$SV = \frac{A \cdot l}{Z_0} \cdot LVET \cdot (dZ/dt)_{max}$$

$$SV = V_{thorax} \cdot LVET \cdot \frac{(dZ/dt)_{max}}{Z_0}$$

Now the resistivity ρ, the determination of which is rather problematic, has been mathematically eliminated from the equation for stroke volume and other hemodynamic parameters. This requires blood resistivity to remain constant during cardiac activity. According to Shankar et al. (see "The Contribution of Vessel Volume Change and Resistivity Change to the Electrical Impedance Pulse," *IEEE Trans Biomed Engl*, BME32:192. (1985)), resistivity variations depending on cardiac activity are less than 5.5%, which is why the equation is sufficiently accurate.

An alternative would comprise the measurement of p at different times of cardiac activity, e.g. at the time of maximum blood flow, during systoles, as well as at the time of minimum blood flow, at the end of diastoles. Like in impedance cardiography, it is better to monitor impedance variations with respect to time $(dZ/dt)_{max}$ since this value is determined by cardiac activity and thus by the blood amount coming from the heart (SV). The new method is based solely on the characteristic that the blood resistivity p, especially of red blood cells (erythrocytes), varies with an alternating current frequency. At 20 kHz, for instance, electrical resistance of blood is significantly higher than at e.g. 100 kHz, wherein the conductivity of erythrocytes increases even further with higher frequencies because at higher frequencies the erythrocyte membrane acts like an electric capacitor. This characteristic may be used for determining p, or more precisely, the decrease of $(dZ/dt)_{max}$ is a measure for the number of red blood cells, i.e. blood resistivity related to the hematocrit. The higher the decrease of $(dZ/dt)_{max}$ during a rise from a low to a high frequency, the higher the number of red blood cells, since with specific heartbeat, the stroke volume remains unchanged.

$$\rho = f(Hkt) = F\left(\frac{(dZ/dt)_{max\_freq1}}{(dZ/dt)_{max\_freq2}}\right) \quad (13)$$

In the case of nonlinear relations, measurements may also be conducted at more than 2 frequencies, and all functions possibly resulting therefrom may be expressed in the form of a nonlinear regression equation. In both cases (2 frequencies, several frequencies), the function f may be empirically determined by comparison of the measurement results with a conventional determination of the hematocrit Hct.

Another method for determining variations of blood resistance during the cardiac cycle from electrically measured signals is also based on the above technique: Wang, L. et al., (see "Multiple Source of the Impedance Cardiogram Based on 3-D Finite Difference Human Thorax Models," *IEEE Transactions on Biomedical Engineering*, 42(2): 141-148 (Feb. 2, 1995)) have shown that the variation of blood resistivity corresponds to ~25% of impedance variation, i.e. it is a significant measure for the determination of the correct SV. This variation of blood resistivity is a direct measure based on the ratio between the two differentiated impedance signals measured at different frequencies $(dZ/dt)_{freq1}/(dZ/dt)_{freq2}$. Thus, an additional signal $\Delta\rho(t)=(dZ/dt)_{freq1}/(dZ/dt)_{freq2}$ can be continuously obtained, which is a measure for blood resistivity variations during the cardiac cycle. For that purpose, a gliding small slot is put over the cardiac cycle in order to determine $\Delta\rho(t)$ for each of these small slots. Maximum deflection of this signal $\Delta\rho_{max}$ can also be used for determining CO. Thus, it is not absolutely necessary to empirically predetermine the function f.

$$\Delta\rho(t) = \frac{(dZ/dt)_{freq1}}{(dZ/dt)_{freq2}} \quad (14)$$

Another advantage of the method is that a sufficient accurate determination of the $\Delta\rho(t)$ signal according to the above technique also allows for the determination of whether the blood is flowing or not and of what type the flow is. With laminar flow, the resistance decreases due to the orientation of erythrocytes in the flow direction, after which it increases again at higher velocity due to turbulences. From the graph of the continuously measured $\Delta\rho(t)$ values it can only be determined how long the blood flows and whether the blood flow is laminar or turbulent. Thus, LVET (left ventricular ejection time), which is conventionally determined directly from the IGK signal or from the phonocardiogram, may also be determined from the changing p value by means of a measurement.

An accurate determination of blood resistivity ρ, the correct operational length $L_0$ or base impedance $Z_0$, which is a measure for the thorax geometry, is required for determining the correct SV because the electrically participating thorax volume $V_{thorax}$ may be deduced from these values. This electrically participating thorax volume $V_{thorax}$ is the most important measure for determining the SV by means of impedance cardiography, as can be seen from the general IKG equation (12c):

$$SV = V_{thorax} \cdot LVET \cdot \frac{(dZ/dt)_{max}}{Z_0} \qquad (12c)$$

As described above, Kubicek calculated $V_{thorax}$ from the distance between the electrodes L, blood resistivity ρ, and base impedance $Z_0$, Sramek or Bernstein estimated $V_{thorax}$ from standing height H and/or patient weight W. Other "improved" formulas used for different IKG devices even use the patient's age to determine $V_{thorax}$.

As mentioned above, these values or linear dependencies of these values may only be determined from electrically measured values. Thus, $V_{thorax}$ may only be determined from various electrical values as well.

$$V_{thorax} = f(L, \rho, Z_0, H, W) \qquad (15)$$

$$V_{thorax} = f\left(\frac{d}{\frac{Z_{02}}{Z_{01}}-1}, \frac{(dZ/dt)_{max\_freq1}}{(dZ/dt)_{max\_freq2}}, \frac{Z_{freq1}}{Z_{freq2}}, \frac{Z_{freq1}}{Z_{freq3}}, \ldots\right)$$

These values determined solely by means of electrical measurements may not only be introduced into any known formula for determining stroke volume and other hemodynamic parameters, e.g. the formulas by Kubicek, Sramek or Bernstein, but also into any other equation for determining stroke volume and other hemodynamic parameters; this also includes nonderived, empirically determined equations that are obtained by means of comparison with a gold standard, e.g. Fick's invasive principle, thermodilution or the breathing gas technique. This leaves only electrically measured values in the equation, resulting in a much higher accuracy. Here, the quality of individual signals is of secondary importance since measurements may be conducted at each heartbeat, i.e. 70 times per minute, and the values obtained at different heartbeats may be averaged or an accurate template may be determined from the impedance signal.

Similarly, the electrically determined parameters L and ρ may be introduced into any known or newly developed equation for determining stroke volume and other hemodynamic parameters. Furthermore, the plurality of parameters electrically determined in this way may be used for calculating other important parameters of mechanical cardiac function, e.g. ejection fraction, contractility, inotropism and pulmonary pressure and the like.

In our experience, is has proven successful to use empirical formulas for stroke volume and other hemodynamic parameters, e.g. ejection fraction, inotropism and the like, which are obtained by use of gold standards for the above values. Here, the determined values $Z_{01}$, $Z_{02}$, $(dZ/dt)_{max\_freq1}$, $(dZ/dt)_{max\_freq2}$, $Z_{freq1}$, $Z_{freq2}$, $Z_{freq3}$, . . . can preferably be related to the actual stroke volume and other hemodynamic parameters obtained by means of a gold standard technique in a multiple regression analysis and/or neural networks and/or further machine learning algorithms. A gold standard suitable for the actual stroke volume and other hemodynamic parameters would primarily be the Fick principle, thermodilution or the breathing gas technique.

Based on this, a multiple regression equation can be created, which describes the best relation between the above parameters and the actual stroke volumes in a purely empirical way, and thus all inhomogeneities of biological measurements are eliminated, as for instance the fact that the thorax is not a geometrically exactly defined body and that homogeneity of electricity propagation in different tissues in the thorax, such as fat, muscle, rib, skin, lung, vascular bundle and heart, can never be mathematically described with sufficient accuracy. Nonlinearities may also result in a multiple polynomial equation. An important aspect in these formulas is the use of whole-body impedance at several frequencies, e.g. at approximately 1-10 kHz, 40 kHz and 200 kHz and optionally even higher frequencies, because body fluid, extracellular space and intracellular fluid and their relations to thoracic fluid content are thus taken into account. Any electrically measured value that has shown in a partial correlation analysis to have a significant relation to cardiac mechanical performance would enter this formula.

Figure 4A:
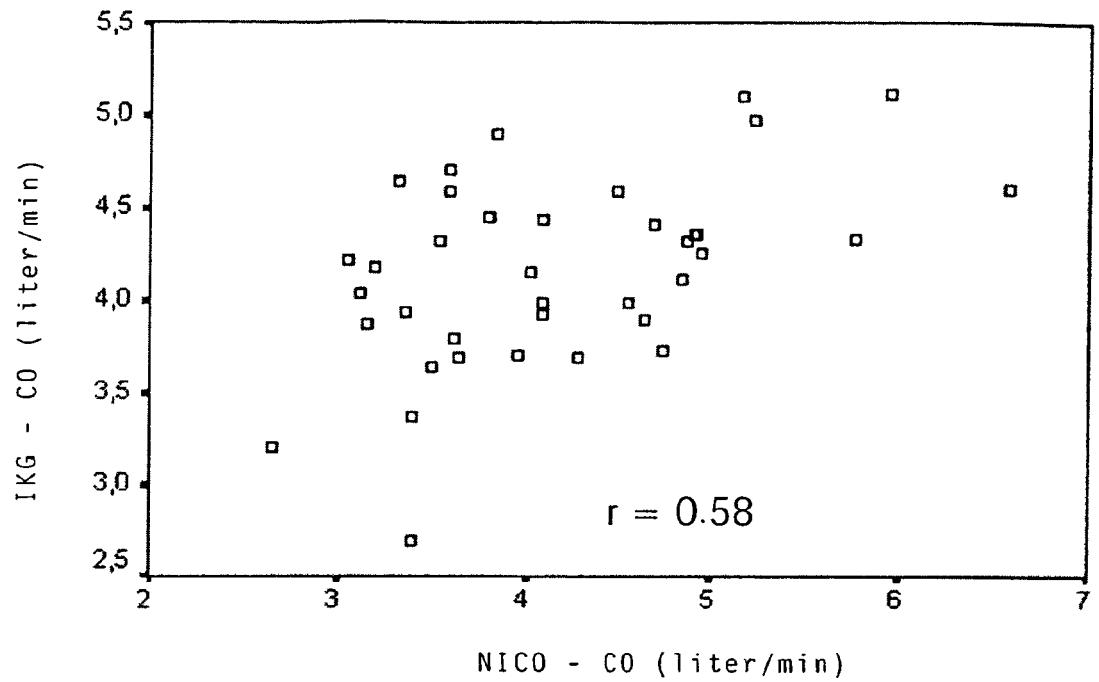
FIG. 4A is a graph showing a comparison between cardiac stroke volume determinations according to conventional impedance cardiography and the rebreathing technique.
Figure 4B:
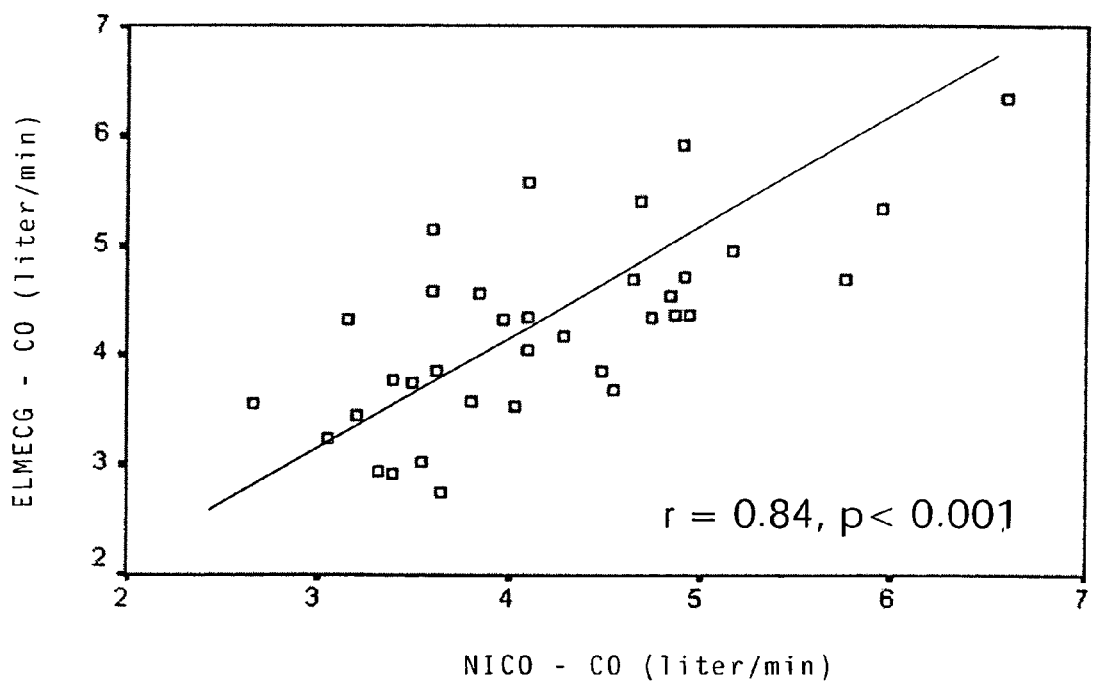
FIG. 4B is a graph showing a comparison between cardiac stroke volume determinations according to impedance cardiography of the present invention (msf-ELMEC) and the rebreathing technique.

FIG. 4, for instance, shows the calculation of CO by means of a simple application of the method described herein in an unselected cohort of individuals, i.e. including patients with cardiac insufficiency that had to be subjected to surgery due to various diseases. During surgery, CO was determined as "gold standard" by means of a NICO device, which measures CO via $CO_2$ rebreathing and shows excellent correspondence with thermodilution. In the upper part of the figure, the x-axis shows the correlation between NICO—CO and conventional impedance cardiography. As can be seen, r is 0.58, constituting a clinically bad and consequently useless correlation (even though the body measures were used, providing a mathematical prediction of CO). The lower part of the figure, on the other hand, shows a comparison between NICO—CO and a very simple embodiment of msf-ELMEC without the use of body parameters, such as weight and height, where the correlation coefficient r is 0.84, constituting a clinically usable correlation. This correlation may be strongly improved in a technically more complex embodiment.

Figure 5:
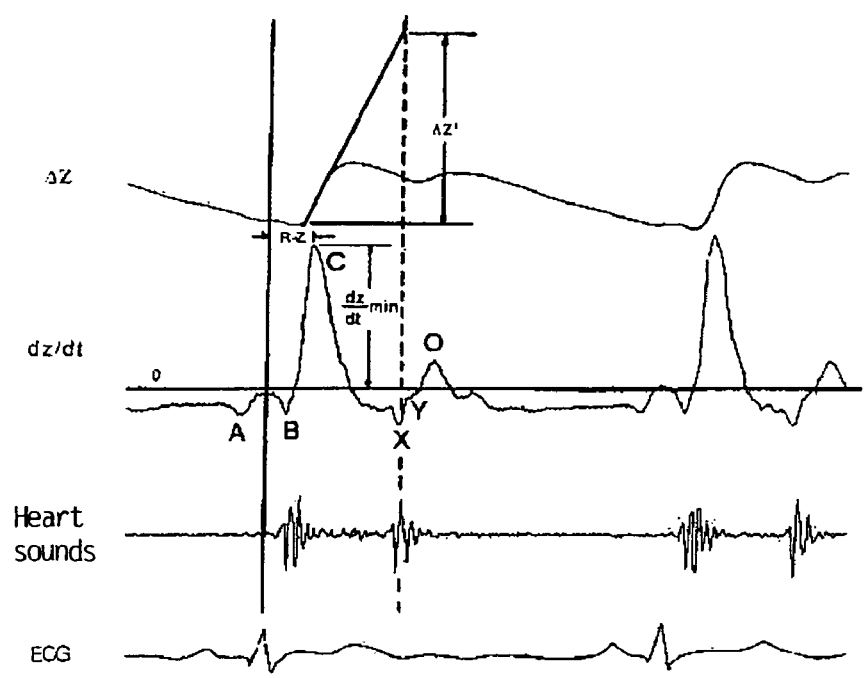
FIG. 5 shows an impedance signal derived with respect to time, an electrocardiogram and a phonocardiogram of a patient.

FIG. 5 shows the conventional impedance signal following the conventional nomenclature, i.e. the times A, B, C, X, Y and O and the simultaneously recorded ECG and phonocardiogram. The time of maximum blood flow is between R-Z and that of minimum blood flow directly before the A wave. It should be kept in mind that conventionally the sign of impedance curves ($\Delta Z$ and $dZ/dt$) is reversed.

Figure 6:
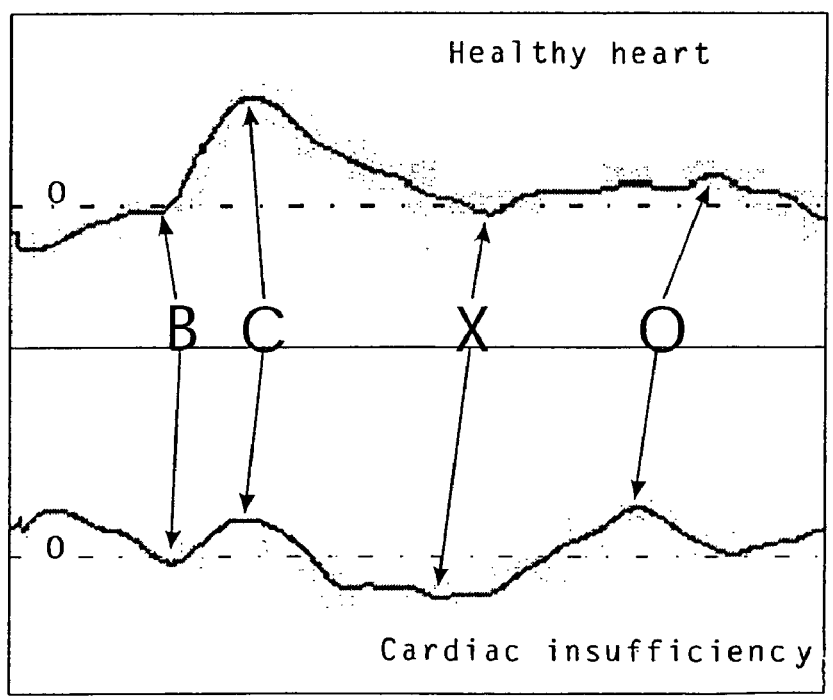
FIG. 6 is a comparison between time-derived impedance signals of a healthy and an ill individual.

Another possibility to improve msf-ELMEC is based on the following approach:

At present, only the height of $dZ/dt$ is used in the interpretation of impedance cardiography, even though the shape of the impedance signal contains much more information. With cardiac insufficiency, for instance, the shape of impedance signals changes as shown in FIG. 6. The upper part of FIG. 6 shows a $dZ/dt$ signal of an individual with a healthy heart, the lower part shows the $dZ/dt$ signal of a patient with cardiac insufficiency. As can be seen, the $(dZ/dt)_{max}$ (C point) decreases, but there are additional changes, such as increases of the amplitudes of the X wave and the O wave.

As can be seen in the figure, instead of using $(dZ/dt)_{max}$ alone, the formula should include the amplitudes of the negative wave B, of the positive Wave C (the real $(dZ/dt)_{max}$), of the negative wave X and of the positive wave O as well as the according rise and fall steepness and the area integrals.

Furthermore, it might be necessary to know the human body's position in space since the different $Z_0$ values at different positions may enter the equation differently. Therefore, it may be advantageous to simultaneously determine the body's position, and for this purpose an angle meter may be attached to the body, the angle meter most preferably being placed in e.g. the distribution element in order to conceal it and allowing reuse with other patients. In this case, the equation for determining stroke volume and other hemodynamic parameters would be corrected for the different body positions.

Thanks to these new developments, the technique is for the first time sufficiently physically accurate, exclusively electrically defined, highly precise and reproducible and therefore for the first time suitable for the diagnosis of cardiac diseases and for monitoring for intensive care and anesthesia purposes. Unlike all other techniques, this one requires the placement of only a few, comfortable electrical electrodes at the thorax and the extremities, which are simultaneously used for the implementation of ECGs; it is no longer necessary to conduct questionable measurements of thorax lengths, which can never be precise because of the thorax's asymmetrical shape and because of the use of multiple electrodes that require averaging; the patient's standing height does no longer have to be entered, which, as mentioned above, introduces a bias favoring errors into the equation; the patient does no longer have to have a catheter introduced into the pulmonary artery or another artery and he does no longer have to breath through a mouthpiece and in a closes system.

Furthermore, the application of a dye, which is measured transcutaneously, becomes unnecessary.

FIG. 7 shows an example of the required electrode elements of the present invention. Thereon, a first current electrode 70 has an electrical terminal 90 for impressing an alternating measuring current, while a first voltage electrode 73 spaced therefrom has a voltage terminal 93 for sensing an electrical measuring current.

According to the present invention, a second voltage electrode 72 with a voltage terminal 92 is provided, which is positioned in a distance d from the first voltage electrode 73. Furthermore, the provision of further voltage electrodes or further current electrodes is also within the scope of the present invention.

The first voltage electrode 73 and the first current electrode 70 as well as the at least one further voltage electrode 72 are provided as parallel, electroconductive strips, which are arranged on a common, electrically insulating carrier material, most preferably a carrier sheet 2. The first voltage electrode 73 and the first current electrode 70 as well as the second voltage electrode 72 are secured on one side of the carrier sheet and preferably provided with an electroconductive adhesive layer.

In order to simplify the establishment of electrical contact with a measuring current source or a measuring voltage device, the carrier sheet 2 is tapered on one longitudinal end to a plug-type surface 6, on which the first voltage electrode 73 and the first current electrode 70 as well as the second voltage electrode 72 are closely spaced. Preferably, the carrier sheet 2 is made of a skin-compatible, nonconductive, flexible material that may be continuously provided between the electrodes 70, 72, 73, as is shown in the embodiment of FIG. 7.

Figure 8:
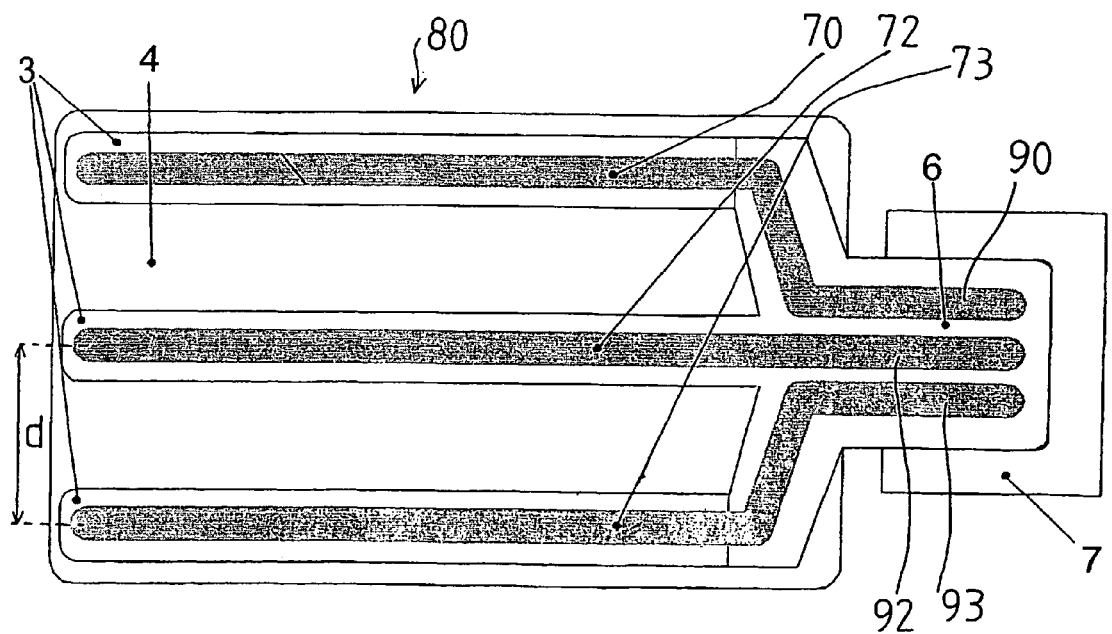
FIG. 8 is a schematic view of another embodiment of the electrode element of the present invention.

In the embodiment of FIG. 8, on the other hand, the carrier material comprises several sheet strips 3 with adhesive surfaces, on which the first voltage electrode 73 and the first current electrode 70 as well as the at least one further voltage electrode 72 are secured, wherein the sheet strips 3 with the electrodes 70, 72, 73 adhere to a common base carrier sheet 4 in a substantially parallel arrangement, which base carrier sheet 4 may be pulled off from the body surface after attaching the sheet strips thereto.

A constant distance between the electrodes 70, 72, 73 is guaranteed by the fact that the base carrier sheet 4 is peeled off after their attachment to the thorax. This has the advantage that skin irritations, such as those caused by the large surface of a very broad carrier sheet 2 of the embodiment according to FIG. 7, are reduced to a very small area.

Initially, the electrode element 80 of the present invention shown in FIG. 8 has a stripping sheet, preferably on the side facing the body, which keeps the conductive coating of the electrodes 70, 72, 73 and the nonconductive adhesive of the base carrier sheet 4 moist and is pulled off directly before use, as is generally known from all medical electrodes.

Of course, further voltage and current electrodes may be attached to the carrier sheet 4, such as an additional current electrode or additional voltage electrodes, in order to enable an even more accurate mathematical calculation of the operational electrode measuring length $L_0$ or the operational distance $d_0$. The use of a common current electrode 70, on the other hand, has the advantage that the electrical field in the thorax cannot change in its inhomogeneity, neither during the measurement of $Z_{01}$ nor of $Z_{02}$.

Another embodiment of the electrode element of the present invention for guaranteeing the constant distance may comprise the attachment of another carrier sheet on the side facing away from the body, which is only pulled off after the finger-shaped carrier sheet has been secured on the thorax. Thus, the surface between the carrier sheets should also not have a skin-irritative adhesive.

As can be seen in FIG. 8, the electrodes 70, 72, 73 are brought together in the area of a plug connection 7 for an impedance measuring device, preferably in a lateral tapering 6 of the sheet strips 3, so that a narrow plug connection 7 can be used which is practicable in clinical daily routine and inexpensive.

FIG. 9 shows a measurement setup on the body of a patient including the measuring system of the present invention. At the distal ends of extremities, such as arms and legs, the electrode elements 7 and 8a are attached, which serve for measuring whole-body impedance at most suitably two, three ore more frequencies and comprise current as well as voltage electrodes. In order zu avoid asymmetric current distribution within the body, in the shown implementation example the electrode elements 7 and 8a are attached to both legs and both arms, wherein the impressed currents are equal in both body halves. Alternatively, a measuring current may be introduced via one arm or one leg only.

Furthermore, the two triple electrode elements 81, 82 are placed at the inferior thoracic aperture and the triple electrode element 80 is attached in the neck area, each comprising one voltage electrode and two current electrodes. Via the current electrode at the upper (neck area) triple electrode element 80 and the current electrode of the lower electrode element 81 at the inferior thoracic aperture as well as between the current electrode of the upper triple electrode element 80 and the lower triple electrode element 82, a measuring current is impressed, wherein the measuring current flowing through the left body half and the measuring current flowing through the right body half are preferably equal. By attaching the left and right lower electrode elements 81, 82, a relatively large body volume is included in the measurement. Alternatively, only one electrode element covering the entire body front at the inferior thoracic aperture may be provided, however, it has been shown that two electrode elements 81, 82 arranged side by side, as shown in FIG. 9, provide better reproducibility of the measurement results. The measuring voltages are sensed at the respective first and second voltage electrodes of the electrode element 80, 81, 82 and processed for determining hemodynamic parameters according to the present invention.

All terminals of the electrode elements 7, 8a, 80, 81, 82 (as well as the electrode elements 80', 81', 82', 85, 85', 85" of FIG. 10) are brought together via connecting leads 10 in a distribution element 9, which is secured to the patient's body and comprises an angle meter 11 for determining the position of the patient's body with respect to the horizontal in order to record its effects on the measurement results. The angle meter 11 may also be placed somewhere else on the patient's body or on the bed, on which the patient is located. A measuring device for determining the impedance 12 is, via a measuring and control line 10a, which is connected to the distribution element 9, able to automatically control all operation modes of the voltage electrodes and also of the current electrodes of the electrode elements 7, 8a, 80, 81, 82, 85, e.g. by means of an analog switch 13.

In addition to a first and a second voltage electrode, the electrode elements 80, 81, 82, 81', 82', 85', 85" may have a third voltage electrode or further voltage electrode.

It is also possible to secure three or more generally known circular electrodes on the body or to aim at a triple or multiple implementation of spot electrodes. Any other electrode form would also have to be implemented in a way to obtain a variable distance, at least between the current or voltage electrodes.

Another example of an electrode arrangement for feeding power into the periphery is shown in FIG. 10. Here, the two triple electrode elements 81, 82 at the inferior thoracic aperture of the embodiment according to FIG. 9 may be replaced by corresponding double electrode elements 81', 82' as long as the current is still peripherally introduced via an electrode 7, however, these double electrode elements 81', 82' must be operated as double voltage electrodes in order to measure the impedance of the substantially identical thorax segment at two different distances.

Additionally, FIG. 10 shows another double electrode element 85, which is optionally placed at the lower end of the trunk approximately at crotch height. Alternatively, FIG. 10a shows the placement of a triple electrode element 85' at the lower end of the trunk, where the current may alternatively be introduced so that impedance variations along the trunk may be measured for two different distances. This electrode element 85 or 85' can be implemented as double or triple electrode element, which is to be short-circuited if necessary, placed on the left and right side of the trunk or on only one side of the trunk. This electrode arrangement has the advantage that it also allows for the measurement of the impedance of extremities for two different distances so that an operational length or an electrically participating volume can be calculated.

This may also be combined with e.g. an optional tourniquet 86 at the extremity in order to plethysmographically measure arterial and venous circulation in a known manner. For measuring venous circulation, the tourniquet has to be inflated to approximately 40 mmHg, which is below arterial pressure, but above venous pressure, in order to calculate the leg's volume increase from the impedance variation. For measuring arterial circulation, the tourniquet has to be inflated above arterial blood pressure, after which the tourniquet is released and impedance variations are analyzed. This constitutes an enormous improvement of the technique, which until now gave circulation changes only as percentage of impedance variation. By means of the calculated, electrically participating volume, volume variations can now also be given in absolute volumes, e.g. in milliliters. Since both legs have substantially the same volumes, double-sided measurements on both legs may also be omitted, and the electrode element 7 may be attached to the periphery of only one extremity, as is shown in FIG. 10. This single electrode element may then be combined with a single electrode element 85 or 85', or, as is shown in FIG. 10b, with a double spot electrode element 85". If the impedance of the legs is not relevant, an electrode element 7, which comprises only one current electrode, but no voltage electrode, may be provided. The arm electrodes may be omitted as well, as is shown in FIG. 10.

This is possible because the arms comprise only a small and highly constant part of the electroconductive body fluids so that even without directly measuring arms, whole-body impedance and thus total body fluid may be extrapolated from measurements on the rest of the body. This has the advantage that the patient, even though he is monitored by means of the method and apparatus according to the present application, is free to use his arms, which are also available for further medical treatments, which is especially appreciated in intensive care units. Consequently, whenever the upper body end is mentioned in the present application, it includes optionally the neck, the superior thoracic aperture, the arms and the head.

Furthermore, the left and/or right electrode elements 81, 82, 81', 82' at the inferior thoracic aperture may selectively be switched off in order to obtain more information about the direction of blood flow within the thorax and the function of the left and right sides of the heart from resulting changes in the impedance curve. As is generally known, the heart pumps blood to the lower left side into the aorta situated left from the heart so that the largest blood vector goes downward to the left, that vector possibly being recognizable more easily if one of the electrode elements 81, 82, 81', 82' at the inferior thoracic aperture is switched off.

The actual arrangement and implementation of the electrode elements as double or triple electrode elements depends on the respective requirements. The aim always is to get as much information as possible with as few electrode elements as possible. A minimum number of electrodes is especially important in intensive care units, where one possibly has to get by with a double electrode element at the neck 80' and one or two triple electrode elements at the trunk 81.

Another very economic alternative providing maximum information comprises a double electrode element 80' at the neck, two further electrode elements 81', 82' on the left and right sides of the inferior thoracic aperture, and a single double electrode element 85 at one side of the lower end of the trunk and another one at the corresponding end of the same lower extremity 7.

This alternative, which comprises only five double electrode elements and would be suitable for intensive care units, does not only provide for the determination of exact cardiac performance, but also of the fluid distribution in the body, divided into extracellular space and intracellular space, as well as the fluid shift from one body half into the other. The current is always introduced via the electrode element 80' at the upper end of the trunk and the electrode element 7 at the lower extremity. The electrodes of the electrode elements 80', 7, placed towards the body center, as well as two electrodes of the electrode elements 81', 82' and the element 85, respectively, are exclusively operated as voltage electrodes.

Furthermore, the calculation of fluid volumes may also take into account serum sodium. As is generally known, this constitutes the main ion in the extracellular space and is thus decisive for conductivity and impedance. With heart diseases, which constitute one application area for the method and apparatus of the present invention, serum sodium often decreases significantly from a standard value of 140 mmol/liter to as low as 115 mmol/liter so that ionicity and consequently conductivity may decrease by up to 20%. If necessary, this has to be taken into account by entering serum sodium or ionicity into the equations used. However, the hematocrit influences blood conductivity as well, and if it is approximately constant, as is usually the case, variations of serum sodium may also be determined by measuring impedance variations during cardiac activity at various frequencies.

An important application of the method may comprise, in addition to the determination of stroke volume, ejection fraction, diastolic function, pulmonal wedge pressure, whole-body fluid, extracellular space and fluid shift, an indirect calculation of hormone concentration in the blood. Examples are the concentration of the natriuretic peptide, e.g. brain natriuretic peptide, or propeptide, atrial natriuretic peptide, also called ADH. In clinical applications, natriuretic peptides are usually used for screening and diagnosing cardiac insufficiency. The determination requires the taking of blood samples and is very expensive (at the moment approximately 40 euros). Based on the typical number of approximately 20 patients with cardiac diseases per day in an outpatient department, one can easily calculate the amortization time of a single apparatus of the present invention.

Regulation of these hormones is closely related to the fluid balance and the expansion of the heart by these fluids. If the fluid balance and the fluid shift by cardiac activity are known in detail, it is possible to predict the concentration of these hormones in the blood and thus avoid expensive blood analyses. All these parameters of the method of the present invention are determined e.g. empirically by measuring the parameter with the gold standard technique, or, in the case of hormones, by blood analyses on a representative number of patients, and by estimating the parameter of interest on the basis of the measured electrical parameters, e.g. with the aid of multiple regression equations or neural networks, other "machine learning" algorithms or any other "black box" model.

The electrode arrangement of the present invention shows significant differences to the U.S. Pat. No. 5,335,667 of Cha: In this patent, the body is indeed split up into segments for measuring the body composition, however, it is not possible to conduct measurements over different lengths on essentially the same segment, wherefore no electrically operational lengths may be calculated. For this reason, U.S. Pat. No. 5,335,667 still requires circumference measurements and manual length measurements on the segment to be analyzed. This is done by means of a tape measure and a caliper, as shown in FIG. 5 of U.S. Pat. No. 5,335,667.

The present application shows, however, that the segment length measured on the surface has nothing or little to do with the calculated "electrically operational length", as can be seen in FIG. 3. And this is the main advantage of the method of the present invention. As can be seen in FIG. 9 and FIG. 10, despite the enormous informational value of the method of the present invention, the number of electrodes is absolutely practicable, especially because they are implemented as multiple electrodes. Furthermore, the electrode arrangement shown in FIG. 10 has the major advantage that position variations along the longitudinal axis of a body are for the first time automatically recognized because each position variation of the body along the longitudinal axis causes significant fluid shifts. These fluid shifts affect venous return to the heart and thus cardiac performance, and venous insufficiency causes significantly larger fluid shifts along the longitudinal axis when the body is erected so that venous insufficiency may easily recognized. Especially in combination with an angle meter it can easily be determined whether the fluid shift is adequate or inadequate for the given position variation and whether the measured cardiac performance variation is adequate for the measured fluid shift.

These examinations can for instance be easily conducted on a tilting table. Electronic requirements are also minimal because measurements at various frequencies and switching over from one electrode to the other does not require any expensive or complicated devices. Thus, it is also possible to use this apparatus in home care by providing such a device for the patient's home. For this purpose, it would be advantageous to allow for the simultaneous conduction of ECGs. The position of the electrodes on the body, as shown in FIGS. 9 and 10, is perfectly suitable for the conduction of ECGs. The patient may thus be provided with his own cheaper, reusable electrodes. These electrodes may for instance be made of a conductive material and be secured by means of flexible bands, as is known from pulse meters in sports. Into these flexible bands, which may be of a nonconductive material, the conductive material may be incorporated in the form of strips or spots, e.g. as conductive rubber, which is then secured to the body by means of an extendible, openable, circular band. These electrodes can also easily be attached by patients, relatives or nursing staff.

Results do not necessarily have to be processed in the apparatus in the patient's home or do not have to be completely processed by this apparatus, but could for instance be transferred to a central office by radio transmission or a dedicated line, e.g. via telephone or e-mail, where a final evaluation of the results is conducted.

This development known as "telemedicine" is especially relevant for patients with heart diseases, who at the moment require a close-meshed control system in expensive special outpatient departments. Usually, heart patients are brought to expensive facilities by ambulance once a month or more often in order to optimize therapy. Often, prognoses for these heart patients are as bad as or worse than those for cancer patients, and therapy has to be adapted continuously in order to keep the patients alive. Furthermore, overaging has led to a dramatic increase of patients with heart diseases, especially cardiac insufficiency, making heart diseases a national epidemic in industrialized countries. Information on changes, e.g. deterioration of cardiac performance, hyperhydration, and the like, determined by the method and apparatus of the invention and transmitted via telemedicine to a central office, either guarantees that patients are brought to the center early enough or allows for the optimization of therapy via telephone or e-mail, so that check-ups in the center may be omitted when the circulation is all right. Despite the use of new technology, high savings are thus guaranteed. If raw data or data only roughly preprocessed in the patient's apparatus are transmitted to a center, local intelligence in the measuring device 12 may be omitted so that the apparatus can be provided at an even lower price.

The differences between impedance tomography and the method and apparatus of the present invention are easily recognizable because in impedance tomography, a plurality of electrodes are secured at the same height, seen in the longitudinal direction of the body, in order to create an image of the fluid distribution in a plane based on the impedance values in the same plane, and to determine three-dimensional fluid distribution from a plurality of planes. Our method, on the other hand, is not aimed at the reconstruction of a plane or the reconstruction of fluid distributions in space, but at the measurement of fluid shifts along the longitudinal axis, wherein the electrically operational distance is for the first time taken into account.

FIG. 11 shows an exemplary embodiment of a multiple spot electrode 14, wherein the constant distance between electrodes is guaranteed by the fact that the connecting cable between the electrodes is at maximum extension when the electrodes are attached to the body, and that by means of the attachment mode of the electrodes, a variation of the distance between the electrodes along the longitudinal axis of the body is achieved. In order to guarantee that the user really complies with the distance between the electrodes, a relatively rigid spacer 16 may be provided between the electrodes, possibly by providing a rigid connecting cable and using it as electrode spacer 16 so that a constant distance is guaranteed. When calculating an operational difference $d_0$, the electrodes may be placed at any distance from each other and the spacer is unnecessary.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A non-invasive method for measuring the volume, the composition and the movement of electroconductive body fluids, based on the electrical impedance of the body or a body segment, especially for performing electromechanocardiography (ELMEC) or impedance cardiography (IKG) measurements for determining hemodynamic parameters,
    wherein an alternating measuring current of at least one frequency is introduced into the body by means of measuring electrodes attached to the body surface,
    wherein the impedance and temporal variations thereof of essentially the same body segment through which the alternating measuring current flows are measured for at least two different measuring lengths (L, L2, L3, L4, L5), essentially in the longitudinal direction of the body, and
    wherein the impedance is sensed at the thorax close to the inferior and superior thoracic apertures for at least two different measuring lengths (L, L2, L3, L4, L5) of essentially the same body segment.

2. A non-invasive method for measuring the volume, the composition and the movement of electroconductive body fluids, based on the electrical impedance of the body or a body segment, especially for performing electromechanocardiography (ELMEC) or impedance cardiography (IKG) measurements for determining hemodynamic parameters,
    wherein an alternating measuring current of at least one frequency is introduced into the body by means of measuring electrodes attached to the body surface,
    wherein the impedance and temporal variations thereof of essentially the same body segment through which the alternating measuring current flows are measured for at least two different measuring lengths (L, L2, L3, L4, L5), essentially in the longitudinal direction of the body, and
    wherein the electrical current is introduced at or close to the upper body end, such as at the neck, head, arms, and the lower body end, such as at a leg or legs, and that the impedance is measured at the thorax and/or trunk for at least two different measuring lengths (L, L2, L3, L4, L5).

3. A non-invasive method for measuring the volume, the composition and the movement of electroconductive body fluids, based on the electrical impedance of the body or a body segment, especially for performing electromechanocardiography (ELMEC) or impedance cardiography (IKG) measurements for determining hemodynamic parameters,
    wherein an alternating measuring current of at least one frequency is introduced into the body by means of measuring electrodes attached to the body surface,
    wherein the impedance and temporal variations thereof of essentially the same body segment through which the alternating measuring current flows are measured for at least two different measuring lengths (L, L2, L3, L4, L5), essentially in the longitudinal direction of the body, and
    wherein the impedance of at least one lower extremity is sensed for at least two different measuring lengths (L, L2, L3, L4, L5) of essentially the same body segment.

4. A non-invasive method for measuring the volume, the composition and the movement of electroconductive body fluids, based on the electrical impedance of the body or a body segment, especially for performing electromechanocardiography (ELMEC) or impedance cardiography (IKG) measurements for determining hemodynamic parameters,
    wherein an alternating measuring current of at least one frequency is introduced into the body by means of measuring electrodes attached to the body surface,
    wherein the impedance and temporal variations thereof of essentially the same body segment through which the alternating measuring current flows are measured for at least two different measuring lengths (L, L2, L3, L4, L5), essentially in the longitudinal direction of the body, and
    wherein additionally whole-body impedance between the lower and upper body end is measured.

5. A non-invasive method for measuring the volume, the composition and the movement of electroconductive body fluids, based on the electrical impedance of the body or a body segment, especially for performing electromechanocardiography (ELMEC) or impedance cardiography (IKG) measurements for determining hemodynamic parameters,
    wherein an alternating measuring current of at least one frequency is introduced into the body by means of measuring electrodes attached to the body surface,
    wherein the impedance and temporal variations thereof of essentially the same body segment through which the alternating measuring current flows are measured for at least two different measuring lengths (L, L2, L3, L4, L5), essentially in the longitudinal direction of the body, and
    wherein the length difference (d, d1, a, a1) between the two different measuring lengths is small compared to the length of the examined body part.

6. The method according to claim 5, wherein the ratio of the length of the examined body part to the length difference (d, d1, a, a1) is between 3:1 and 30:1.

7. The method according to claim 6, wherein the ratio of the length of the examined body part to the length difference (d, d1, a, a1) is approximately 10:1.

8. A non-invasive method for measuring the volume, the composition and the movement of electroconductive body fluids, based on the electrical impedance of the body or a body segment, especially for performing electromechanocardiography (ELMEC) or impedance cardiography (IKG) measurements for determining hemodynamic parameters,
    wherein an alternating measuring current of at least one frequency is introduced into the body by means of measuring electrodes attached to the body surface,
    wherein the impedance and temporal variations thereof of essentially the same body segment through which the alternating measuring current flows are measured for at least two different measuring lengths ((L, L2, L3, L4, L5), essentially in the longitudinal direction of the body, and
    wherein from the impedance values determined for different measuring lengths (L, L2, L3, L4, L5) between electrodes, an operational electrode measuring length (L0), which corresponds to the electrically operational length of the body segment, and optionally an operational electrode distance (d0) are calculated.

9. The method according to claim 8, wherein the electrically operational length of the body segment is calculated according to the formula $L0=d/(Z02/Z01-1)$, where d is the difference between the two electrode measuring lengths used for the measurement, $Z02$ is the impedance for the longer electrode measuring length, and $Z01$ is the impedance for the shorter electrode measuring length.

10. A non-invasive method for measuring the volume, the composition and the movement of electroconductive body fluids, based on the electrical impedance of the body or a body segment, especially for performing electromechanocardiography (ELMEC) or impedance cardiography (IKG) measurements for determining hemodynamic parameters,
    wherein an alternating measuring current of at least one frequency is introduced into the body by means of measuring electrodes attached to the body surface,
    wherein the impedance and temporal variations thereof of essentially the same body segment through which the alternating measuring current flows are measured for at least two different measuring lengths (L, L2, L3, L4, L5), essentially in the longitudinal direction of the body,
    wherein the impedance is sensed at the thorax close to the inferior and superior thoracic apertures for at least two different measuring lengths (L, L2, L3, L4, L5) of essentially the same body segment, and
    wherein voltage electrodes at the inferior thoracic aperture are provided as double electrodes on the left and right side, respectively, of the thorax, wherein electrodes positioned at the same distance in the longitudinal direction are electrically connected to each other.

11. The method according to claim 10, wherein the electrodes on the left and right side, respectively, of the thoracic aperture may selectively be switched off.

12. A non-invasive method for measuring the volume, the composition and the movement of electroconductive body fluids, based on the electrical impedance of the body or a body segment, especially for performing electromechanocardiography (ELMEC) or impedance cardiography (IKG) measurements for determining hemodynamic parameters,
    wherein an alternating measuring current of at least one frequency is introduced into the body by means of measuring electrodes attached to the body surface,
    wherein the impedance and temporal variations thereof of essentially the same body segment through which the alternating measuring current flows are measured for at least two different measuring lengths (L, L2, L3, L4, L5), essentially in the longitudinal direction of the body,
    wherein the electrical current is introduced at or close to the upper body end, such as at the neck, head, arms, and the lower body end, such as at a leg or legs, and that the impedance is measured at the thorax and/or trunk for at least two different measuring lengths (L, L2, L3, L4, L5), and
    wherein measuring electrodes at the lower end of the trunk are provided as double electrodes on the left and right side, respectively, of the lower end of the trunk, wherein electrodes positioned at the same distance in the longitudinal direction are electrically connected to each other.

13. The method according to claim 12, wherein the electrodes on the left and right side, respectively, of the lower end of the trunk may selectively be switched off.

14. A non-invasive method for measuring the volume, the composition and the movement of electroconductive body fluids, based on the electrical impedance of the body or a body segment, especially for performing electromechanocardiography (ELMEC) or impedance cardiography (IKG) measurements for determining hemodynamic parameters,
    wherein an alternating measuring current of at least one frequency is introduced into the body by means of measuring electrodes attached to the body surface,
    wherein the impedance and temporal variations thereof of essentially the same body segment through which the alternating measuring current flows are measured for at least two different measuring lengths (L, L2, L3, L4, L5), essentially in the longitudinal direction of the body, and
    wherein impedance variations with respect to time are measured at at least two frequencies.

15. The method according to claim 14, wherein the impedance is measured at three different frequencies.

16. The method according to claim 15, wherein the different frequencies are between 1 and 10 kHz, approximately 30 and 100 kHz, and above 200 kHz.

17. A non-invasive method for measuring the volume, the composition and the movement of electroconductive body fluids, based on the electrical impedance of the body or a body segment, especially for performing electromechanocardiography (ELMEC) or impedance cardiography (IKG) measurements for determining hemodynamic parameters,
    wherein an alternating measuring current of at least one frequency is introduced into the body by means of measuring electrodes attached to the body surface,
    wherein the impedance and temporal variations thereof of essentially the same body segment through which the alternating measuring current flows are measured for at least two different measuring lengths (L, L2, L3, L4, L5), essentially in the longitudinal direction of the body, and
    wherein a maximum temporal variation of the measured impedance values (dZ/dt) is determined at at least two different measuring frequencies, and that the resistivity of the blood present in the body is determined therefrom.

18. The method according to claim 17, wherein the maximum temporal variation of the measured impedance value, especially in relatively small time frames, is determined at different times of the cardiac cycle.

19. The method according to claim 18, wherein the time frames are set at an abrupt rise of resistivity and at the time of minimum blood flow at the end of a diastole.

20. The method according to claim 18, wherein the time slots are put over the total cardiac cycle as small gliding slots.

21. A non-invasive method for measuring the volume, the composition and the movement of electroconductive body fluids, based on the electrical impedance of the body or a body segment, especially for performing electromechanocardiography (ELMEC) or impedance cardiography (IKG) measurements for determining hemodynamic parameters,
    wherein an alternating measuring current of at least one frequency is introduced into the body by means of measuring electrodes attached to the body surface,
    wherein the impedance and temporal variations thereof of essentially the same body segment through which the alternating measuring current flows are measured for at least two different measuring lengths (L, L2, L3, L4, L5), essentially in the longitudinal direction of the body,
    wherein the impedance variations with respect to time are measured at at least two frequencies, and
    wherein the frequency of the alternating measuring current is continuously varied from a lower measuring frequency to a higher measuring frequency.

22. The method according to claim 21, wherein the lower measuring frequency is approximately 1 kHz and the higher measuring frequency approximately 1000 kHz.

23. A non-invasive method for measuring the volume, the composition and the movement of electroconductive body fluids, based on the electrical impedance of the body or a body segment, especially for performing electromechanocardiography (ELMEC) or impedance cardiography (IKG) measurements for determining hemodynamic parameters,
  wherein an alternating measuring current of at least one frequency is introduced into the body by means of measuring electrodes attached to the body surface,
  wherein the impedance and temporal variations thereof of essentially the same body segment through which the alternating measuring current flows are measured for at least two different measuring lengths (L, L2, L3, L4, L5), essentially in the longitudinal direction of the body,
  wherein the impedance variations with respect to time are measured at at least two frequencies, and
  wherein the measuring current is impressed for at least another current electrode distance and at several different measuring frequencies, and that the impedance is measured for the different voltage measuring lengths and at the different frequencies.

24. A non-invasive method for measuring the volume, the composition and the movement of electroconductive body fluids, based on the electrical impedance of the body or a body segment, especially for performing electromechanocardiography (ELMEC) or impedance cardiography (IKG) measurements for determining hemodynamic parameters,
  wherein an alternating measuring current of at least one frequency is introduced into the body by means of measuring electrodes attached to the body surface,
  wherein the impedance and temporal variations thereof of essentially the same body segment through which the alternating measuring current flows are measured for at least two different measuring lengths (L, L2, L3, L4, L5), essentially in the longitudinal direction of the body, and
  wherein the phase angle between measuring current and measuring voltage is determined.

25. A non-invasive method for measuring the volume, the composition and the movement of electroconductive body fluids, based on the electrical impedance of the body or a body segment, especially for performing electromechanocardiography (ELMEC) or impedance cardiography (IKG) measurements for determining hemodynamic parameters,
  wherein an alternating measuring current of at least one frequency is introduced into the body by means of measuring electrodes attached to the body surface,
  wherein the impedance and temporal variations thereof of essentially the same body segment through which the alternating measuring current flows are measured for at least two different measuring lengths (L, L2, L3, L4, L5), essentially in the longitudinal direction of the body, and
  wherein amplitudes, areas, and ascending or descending tangents of the impedance waves are used independently or together for calculating hemodynamic parameters.

26. A non-invasive method for measuring the volume, the composition and the movement of electroconductive body fluids, based on the electrical impedance of the body or a body segment, especially for performing electromechanocardiography (ELMEC) or impedance cardiography (IKG) measurements for determining hemodynamic parameters,
  wherein an alternating measuring current of at least one frequency is introduced into the body by means of measuring electrodes attached to the body surface,
  wherein the impedance and temporal variations thereof of essentially the same body segment through which the alternating measuring current flows are measured for at least two different measuring lengths (L, L2, L3, L4, L5), essentially in the longitudinal direction of the body, and
  wherein empirical equations that have been determined by means of a gold standard including one of the Fick principle for stroke volume and e.g. echocardiography or isotope methods for other parameters, including as ejection fraction, pulmonal wedge pressure, diastolic function and the like, are used for measuring hemodynamic parameters.

27. A non-invasive method for measuring the volume, the composition and the movement of electroconductive body fluids, based on the electrical impedance of the body or a body segment, especially for performing electromechanocardiography (ELMEC) or impedance cardiography (IKG) measurements for determining hemodynamic parameters,
  wherein an alternating measuring current of at least one frequency is introduced into the body by means of measuring electrodes attached to the body surface,
  wherein the impedance and temporal variations thereof of essentially the same body segment through which the alternating measuring current flows are measured for at least two different measuring lengths (L, L2, L3, L4, L5), essentially in the longitudinal direction of the body, and
  wherein the sodium content in serum is determined and used in the calculation of relevant parameters.

28. A non-invasive method for measuring the volume, the composition and the movement of electroconductive body fluids, based on the electrical impedance of the body or a body segment, especially for performing electromechanocardiography (ELMEC) or impedance cardiography (IKG) measurements for determining hemodynamic parameters,
  wherein an alternating measuring current of at least one frequency is introduced into the body by means of measuring electrodes attached to the body surface,
  wherein the impedance and temporal variations thereof of essentially the same body segment through which the alternating measuring current flows are measured for at least two different measuring lengths (L, L2, L3, L4, L5), essentially in the longitudinal direction of the body, and
  wherein the sodium concentration in serum is mathematically estimated by the method and obtained as a result.

29. A non-invasive method for measuring the volume, the composition and the movement of electroconductive body fluids, based on the electrical impedance of the body or a body segment, especially for performing electromechanocardiography (ELMEC) or impedance cardiography (IKG) measurements for determining hemodynamic parameters,
  wherein an alternating measuring current of at least one frequency is introduced into the body by means of measuring electrodes attached to the body surface,
  wherein the impedance and temporal variations thereof of essentially the same body segment through which the alternating measuring current flows are measured for at least two different measuring lengths (L, L2, L3, L4, L5), essentially in the longitudinal direction of the body, and
  wherein hormones, including one of ADH and natriuretic peptide, especially brain natriuretic peptide, and precursors thereof regulating body fluids, fractions and the composition thereof, are estimated by means of empirical equations and obtained as a result.

30. A non-invasive method for measuring the volume, the composition and the movement of electroconductive body fluids, based on the electrical impedance of the body or a body segment, especially for performing electromechanocardiography (ELMEC) or impedance cardiography (IKG) measurements for determining hemodynamic parameters, wherein an alternating measuring current of at least one frequency is introduced into the body by means of measuring electrodes attached to the body surface, wherein the impedance and temporal variations thereof of essentially the same body segment through which the alternating measuring current flows are measured for at least two different measuring lengths (L, L2, L3, L4, L5), essentially in the longitudinal direction of the body, and wherein results of the measurements are sent to a central station in digital form by one of telephone and e-mail where the results are further processed and assessed, whereafter all necessary measures and therapy changes are transmitted to the patient from a remote place.

31. A non-invasive method for measuring the volume, the composition and the movement of electroconductive body fluids, based on the electrical impedance of the body or a body segment, especially for performing electromechanocardiography (ELMEC) or impedance cardiography (IKG) measurements for determining hemodynamic parameters, wherein an alternating measuring current of at least one frequency is introduced into the body by means of measuring electrodes attached to the body surface, wherein the impedance and temporal variations thereof of essentially the same body segment through which the alternating measuring current flows are measured for at least two different measuring lengths (L, L2, L3, L4, L5), essentially in the longitudinal direction of the body, and wherein the body fluid is determined with its fractions, including extracellular space and intracellular space, and read out.

* * * * *